US009631180B2

(12) United States Patent
Tebo et al.

(10) Patent No.: US 9,631,180 B2
(45) Date of Patent: Apr. 25, 2017

(54) RECOMBINANT MANGANESE OXIDASE

(71) Applicants: Bradley M. Tebo, Portland, OR (US); Cristina Butterfield, Berkeley, CA (US)

(72) Inventors: Bradley M. Tebo, Portland, OR (US); Cristina Butterfield, Berkeley, CA (US)

(73) Assignee: OREGON HEALTH & SCIENCE UNIVERSITY, Portland, OR (US)

( * ) Notice: Subject to any disclaimer, the term of this patent is extended or adjusted under 35 U.S.C. 154(b) by 0 days.

(21) Appl. No.: 14/816,328

(22) Filed: Aug. 3, 2015

(65) Prior Publication Data

US 2016/0017297 A1 Jan. 21, 2016

Related U.S. Application Data

(63) Continuation of application No. 14/208,915, filed on Mar. 13, 2014, now abandoned.

(60) Provisional application No. 61/779,729, filed on Mar. 13, 2013.

(51) Int. Cl.
*C12N 9/08* (2006.01)
*C12N 9/02* (2006.01)

(52) U.S. Cl.
CPC ......... *C12N 9/0065* (2013.01); *C12N 9/0004* (2013.01); *C12N 9/0091* (2013.01); *C12Y 111/01013* (2013.01)

(58) Field of Classification Search
CPC .................................................... C12N 9/0065
USPC ......................................................... 435/183
See application file for complete search history.

(56) References Cited

U.S. PATENT DOCUMENTS

| | | | | |
|---|---|---|---|---|
| 6,277,622 | B1 * | 8/2001 | Weiss | C12N 9/0022 435/183 |
| 8,178,090 | B2 * | 5/2012 | Stougaard | A01N 63/00 424/401 |
| 2006/0057633 | A1 * | 3/2006 | Cervin | C12N 15/1082 435/7.1 |

OTHER PUBLICATIONS

Dick et al., Applied and Environmental Microbiology, vol. 74(5), 1527-1534, 2008.*

* cited by examiner

*Primary Examiner* — Maryam Monshipouri
(74) *Attorney, Agent, or Firm* — Jeffrey M. Jackson

(57) ABSTRACT

Disclosed herein is a recombinant *Bacillus* manganese oxidase complex, including a bacterial expression vector for the expression of the complex and a method of synthesizing the complex.

8 Claims, 7 Drawing Sheets

SEQUENCE LISTING

```
<160> NUMBER OF SEQ ID NOS: 10

<210> SEQ ID NO 1
<211> LENGTH: 5161
<212> TYPE: DNA
<213> ORGANISM: Bacillus sp.

<400> SEQUENCE: 1

atgcgtcatt cggattattt gaaaaatttg ttagagaaca gaaggaatga agtcaggcag      60
gtagatccta ttcacgaagt agggaatcat atcacctctc caccaagtgc aacatcacta     120
gaagagaata aaatcattgc cgaatacctg gaacaaaaaa atcttcacac actggcgaat     180
gctgttcctg aatttaaaaa accattgatt ttaaagaagt tttttaagat gaagcggaat     240
caggaagtta tagtctatat tgaccatcaa gataatacac aggaaatctc cggtaaggtg     300
aatgccatcg gtagagattt tgtcatactc acgaacttaa aggatcggat ttggatcccg     360
tataaaacga tattatcagc aaattctcca tctggagtgc cgacatatga aaatgcccat     420
caaaatttca tctatgataa tgacttaaaa cgaaaactga ctacgaattt tggtgaaaca     480
gttgccaatc gagatgtttt aattcagcaa tttttcgaag agtcactaaa aggcaacctt     540
catagatggc aaggagtgtg ggttaaggtg tttttagctg atgaaatagt aatcgggaag     600
atcgcttcgg ttactgagga gtttatccta ttacaatctt ttggctcaga aagggaaatt     660
gccctcacag atgtaactct aattcgttct gcccgccttt ttatccaatt cctgttgatg     720
gggaagaaca tgatcaagag tatgtttcgt taagacataa attgcagaaa ttttatttac     780
aagaaagggt gacaaaacat gcatgactcg ccattaaaat cattatcggc tgcttctaat     840
gtcgctagtg tcaatgaccc attatttgat ttttttaaca agcatatggg caaacaaatc     900
ctgattatta cggaatcatc acaattaaat atattagggc aaaccttcag gccaattttt     960
tgcggaaagg tagctgaagt tgaacctgga catttaacac tttctcccgt aacaatcaaa    1020
attttgaatg caccgtttca taagttccca attccgttat ccattccttt tgaaaaaatt    1080
gcccatttca caacagacgt cgattgttcg atgagaattc cgttagttta aacatacaag    1140
taatggaggc gttgtttcct atgtccacag attactcaaa aatgacagat gtaaatgaaa    1200
tccatgactc agccatcttg gaacacttca gaaatggaat tggccacaaa acgcttgtga    1260
tttctccatc ctatccatat atgttcgttg gcataatcaa ggaattgatc ggtgatacgg    1320
ttatgatcga tgttgagacc acacactttg ctcaattaga aaaccgcgaa tggtacattc    1380
acattcataa tattgaagtt ttctatattg aaaggcctgg agcacctaaa ataccgaagc    1440
tcgaagacta ttagattcct atgaaggggg gaaatacatg ttacgaaaat ttcatgttgt    1500
cggaatttca acgaggatag tagttaatac gttcggggac cataatccta atggcagaat    1560
```

-continued

```
atatgtcttg aaggaaaatg agtcaaagct taaagacctc gtgagaaaga atccttataa   1620
gccaattgat ctcgttcaac cgctggctat tcgcgcaaat gagggggata tagttgaaat   1680
actttttgaa aatcagcttt ctttttcagc aggaatgcac tttcaggaag ctgattacag   1740
tgtgctcagt tccgatggag cggatgccgg atataacccg gatacaacgg tagaacctgg   1800
cggagaaatt ctttacaggc ttaatgtcaa tcaggaaggt atctgcttct tcaccgacct   1860
tggaaatgtt tcaagcaccg aacaaggatc aagtgtccaa gggttattcg gagcactgct   1920
tgtccaaaaa aggggctcta gctggactga tcctgttact ggcggtccaa ttaatagcgg   1980
tgtgtatgct gatatacatc atccttttct gccatctttc agggagtacg catggttctt   2040
caatgacgaa atggaaatta gggatcttac gggggaacgt cccttgaacc caatgacaaa   2100
ccaggaagca gaatcctttc atggagtgaa tcttcgctat gaacctatga cgaaccggaa   2160
aaggctgatg gaggcaggag ttgtatgccc tgattgtgat tcagaagaag ttcatcatga   2220
ctcatgggtg tttggtgatc cggccactcc gatactaagg ggttatgtgg gggatcctgc   2280
agtcatcagg ctgattcatg gcggtgtaaa agaaactcat gtttttcact accatgtcca   2340
tcaatggctc ggtgattcaa gtaatattaa tgcagaaatt cttgatgccc aatccataag   2400
ccctcaaacc cactattcga ttcagccgct ctatggactc ggaagcctgc atggcgccat   2460
cggtgactcc attatccact gccatttgta tccgcacttc ggcataggta tgtggggaat   2520
gaacagggtt tttgatactc tgcaggatgg aagccagtgt tatccgaatg gagtccgaat   2580
taaggcctta atgccattgc cagaccgtcc tgaaccgcca aagccaacac ctgaaaaacc   2640
aggattccct aatttcattc cgggaaaagt cggctacaaa gcaccaaggc cgcctctggg   2700
cattgttgga ggccgggaga tgactgaact ggaacggaat gcagcgattg aaaatccacg   2760
tccaggagcc gttttcgttg acccttgcct agaccaggac ccggtggtag ttgaatttaa   2820
tgtttctgct attgaaatgc cagtcgtata taacaaacag ggctggcatg accctaaagc   2880
aagattttat gtgatggatg aagacctgga tgatatcctt tcagggaaaa aagagcctga   2940
gccgcttgta ttccatgtcc ctgcaggtac atgtatacgg atgaattata ctaatcgcat   3000
gccgcatatt ttagatggcg atgcattcca gctggtgaca aggacgtatg aaaatggttt   3060
tcacattcac tttgtaaaat ttgatgtcct tgcctgcgat ggaggaaatg taggatggaa   3120
ttatgacagt gctgttcttc ctggccagac cattcgctat gagtggtatg cggaaaccga   3180
attaaaagcg tttttcttcc atgaccatct atttgcaaac tctcaccagc agcatggagt   3240
ttttggtgca ggcgtgatac agccaagatt ttcaaaattc cttgattcga gaactggtga   3300
cgaggtggac catggtaccc agatttccgt cgaacacccg ttaatcccgg attaccgtga   3360
ccagacactt ttcgtccatg attttgccct tttattcgat aaaaacggcc gtccaatcca   3420
gccgccggaa tatcctggtt cagaggatga cccaggtgtc tttggagtca attttaaatg   3480
tgaaccttta aagttcaggc taggtgagga ttgtgaccct gcatattcct tcagttccta   3540
tgttcacggt gatcctgtta ccccgatact gagggcttat gaaggcgacc caatcaggat   3600
caggctgttg cagggagcgc atgaagaatc tcacagcttc aatatccatg ggctgagatg   3660
gaaagaagag cgcccggatt tgggatcatc catgaaagcg cagcagcata tcggaatctc   3720
tgagtccttc acttttgaga ctgagatccc agcatccggt gattatcttt gggcctttga   3780
ggatgaggag gatgtatggc ttggtacatg gggtttgatc cgtgcgtata aaggaagaat   3840
ggaagattta atcgtcttga ctgaccgaga agccctgccg gaaggatccg ctgaaactcc   3900
aaagccaaca gggaaaccgc ctgaaaaagc aaatccactt gccagtctgc ctccgggggc   3960
```

```
ttaccagggc tcacctgtca agaagttcga ggtagtcgcc ttccagacac caatccaata   4020

taactcmtat ggcgatcatg acccatatgg tattattttc gctttaaagg aggatgtaga   4080

agacattctc actggcaaaa agaatccggt gccactaatc ttaagggcta atgtcggtga   4140

ccttgtagaa gtcaccctga caagtgaact gaagaaagag ctctttccat ttcaagatgg   4200

aatccatcct tacccgccgg taaaagaaca atctttttat cctccttcat taaggatatc   4260

tcttcataca agcctgctga attatgacgt taaaacatcc agtggagata cagttggtta   4320

caaccctgac cagactgtcg gtccagggga aacgatcaca tatagatggt ttgtcgatgg   4380

ccagttcggc atgtgttcga tgtgggacat ggccgatctg cgaaatcacc ggtcgtttgg   4440

taccttcggt gcattcgttg ccgagtccag gtttacaact tacctggatc catacagcct   4500

ggaaaaagcc attacagggg aaaatgtgat tcttcggcac cccttacttc ctgctacaag   4560

agaatttgtc ctcattttac atgatggtgt aaggctggag gacaaagatg ggaaagtgat   4620

tattgatccg atggatgggg tggtacctga tactgaagag ctcgaagaag tcgatacgta   4680

cgattatgga tcaaggggtt ttaactaccg cagtgaaaga ctgatcaatc gttataagga   4740

acacccggtt atgcacgagc ttttttcatc agaagttttt ggggacccag cgacaccttt   4800

attcgaggca tatcctggtg aacctgtggt aatgcggatt acgactcctg cagaaaggcg   4860

aagagctcat acattccatc ttcacggaca ttattggaaa tttgacagca aggatcttga   4920

ttctcgtatt cagtcatttt taggccatat ggttacgggc catactgatg atttgcgctt   4980

gattggagga gcaggaggag tattcaattt cccaggggat tacttgtacc ggtcgggcaa   5040

tatccgctgg gacatagaat tggggatgtg ggaatcttc  cgggttcata aggattcgaa   5100

ggaaaacctg ccgcgtcttg aggaagttga agggggtgg  gacaatgaag aaaaggcata   5160

a                                                                   5161


<210> SEQ ID NO 2
<211> LENGTH: 37
<212> TYPE: DNA
<213> ORGANISM: Artificial Sequence
<220> FEATURE:
<223> OTHER INFORMATION: PCR Primer

<400> SEQUENCE: 2

gctagcatgc gtcattcgga ttatttgaaa aatttgt                              37


<210> SEQ ID NO 3
<211> LENGTH: 34
<212> TYPE: DNA
<213> ORGANISM: Artificial Sequence
<220> FEATURE:
<223> OTHER INFORMATION: PCR Primer

<400> SEQUENCE: 3

ctcgagttat gccttttctt cattgtccca cccc                                 34


<210> SEQ ID NO 4
<211> LENGTH: 250
<212> TYPE: PRT
<213> ORGANISM: Bacillus sp.

<400> SEQUENCE: 4

Met Arg His Ser Asp Tyr Leu Lys Asn Leu Leu Glu Asn Arg Arg Asn
1               5                   10                  15

Glu Val Arg Gln Val Asp Pro Ile His Glu Val Gly Asn His Ile Thr
```

-continued

```
            20                  25                  30

Ser Pro Pro Ser Ala Thr Ser Leu Glu Glu Asn Lys Ile Ile Ala Glu
        35                  40                  45

Tyr Leu Glu Gln Lys Asn Leu His Thr Leu Ala Asn Ala Val Pro Glu
    50                  55                  60

Phe Lys Lys Pro Leu Ile Leu Lys Lys Phe Phe Lys Met Lys Arg Asn
65                  70                  75                  80

Gln Glu Val Ile Val Tyr Ile Asp His Gln Asp Asn Thr Gln Glu Ile
                85                  90                  95

Ser Gly Lys Val Asn Ala Ile Gly Arg Asp Phe Val Ile Leu Thr Asn
            100                 105                 110

Leu Lys Asp Arg Ile Trp Ile Pro Tyr Lys Thr Ile Leu Ser Ala Asn
        115                 120                 125

Ser Pro Ser Gly Val Pro Thr Tyr Glu Asn Ala His Gln Asn Phe Ile
    130                 135                 140

Tyr Asp Asn Asp Leu Lys Arg Lys Leu Thr Thr Asn Phe Gly Glu Thr
145                 150                 155                 160

Val Ala Asn Arg Asp Val Leu Ile Gln Gln Phe Phe Glu Glu Ser Leu
                165                 170                 175

Lys Gly Asn Leu His Arg Trp Gln Gly Val Trp Val Lys Val Phe Leu
            180                 185                 190

Ala Asp Glu Ile Val Ile Gly Lys Ile Ala Ser Val Thr Glu Glu Phe
        195                 200                 205

Ile Leu Leu Gln Ser Phe Gly Ser Glu Arg Glu Ile Ala Leu Thr Asp
    210                 215                 220

Val Thr Leu Ile Arg Ser Ala Arg Leu Phe Ile Gln Phe Leu Leu Met
225                 230                 235                 240

Gly Lys Asn Met Ile Lys Ser Met Phe Arg
                245                 250


<210> SEQ ID NO 5
<211> LENGTH: 110
<212> TYPE: PRT
<213> ORGANISM: Bacillus sp.

<400> SEQUENCE: 5

Met His Asp Ser Pro Leu Lys Ser Leu Ser Ala Ala Ser Asn Val Ala
1               5                   10                  15

Ser Val Asn Asp Pro Leu Phe Asp Phe Phe Asn Lys His Met Gly Lys
            20                  25                  30

Gln Ile Leu Ile Ile Thr Glu Ser Ser Gln Leu Asn Ile Leu Gly Gln
        35                  40                  45

Thr Phe Arg Pro Ile Phe Cys Gly Lys Val Ala Glu Val Glu Pro Gly
    50                  55                  60

His Leu Thr Leu Ser Pro Val Thr Ile Lys Ile Leu Asn Ala Pro Phe
65                  70                  75                  80

His Lys Phe Pro Ile Pro Leu Ser Ile Pro Phe Glu Lys Ile Ala His
                85                  90                  95

Phe Thr Thr Asp Val Asp Cys Ser Met Arg Ile Pro Leu Val
            100                 105                 110


<210> SEQ ID NO 6
<211> LENGTH: 103
<212> TYPE: PRT
<213> ORGANISM: Bacillus sp.
```

-continued

<400> SEQUENCE: 6

Met Glu Ala Leu Phe Pro Met Ser Thr Asp Tyr Ser Lys Met Thr Asp
1 5 10 15

Val Asn Glu Ile His Asp Ser Ala Ile Leu Glu His Phe Arg Asn Gly
20 25 30

Ile Gly His Lys Thr Leu Val Ile Ser Pro Ser Tyr Pro Tyr Met Phe
35 40 45

Val Gly Ile Ile Lys Glu Leu Ile Gly Asp Thr Val Met Ile Asp Val
50 55 60

Glu Thr Thr His Phe Ala Gln Leu Glu Asn Arg Glu Trp Tyr Ile His
65 70 75 80

Ile His Asn Ile Glu Val Phe Tyr Ile Glu Arg Pro Gly Ala Pro Lys
85 90 95

Ile Pro Lys Leu Glu Asp Tyr
100

<210> SEQ ID NO 7
<211> LENGTH: 299
<212> TYPE: PRT
<213> ORGANISM: Bacillus sp.

<400> SEQUENCE: 7

His Val Phe His Tyr His Val His Gln Trp Leu Gly Asp Ser Ser Asn
1 5 10 15

Ile Asn Ala Glu Ile Leu Asp Ala Gln Ser Ile Ser Pro Gln Thr His
20 25 30

Tyr Ser Ile Gln Pro Leu Tyr Gly Leu Gly Ser Leu His Gly Ala Ile
35 40 45

Gly Asp Ser Ile Ile His Cys His Leu Tyr Pro His Phe Gly Ile Gly
50 55 60

Met Trp Gly Ile Asn Arg Val Phe Asp Thr Leu Gln Asp Gly Ser Gln
65 70 75 80

Cys Tyr Pro Asn Gly Val Arg Ile Asp Ala Leu Lys Pro Leu Pro Asp
85 90 95

Arg Pro Ala Pro Pro Lys Pro Thr Arg Glu Lys Pro Gly Phe Pro Asn
100 105 110

Phe Ile Pro Gly Lys Val Gly Tyr Lys Ala Pro Arg Pro Pro Leu Gly
115 120 125

Ile Val Gly Gly Arg Glu Met Thr Glu Leu Glu Arg Asn Ala Ala Ile
130 135 140

Pro Asn Pro Arg Pro Gly Ala Val Phe Val Asp Pro Cys Leu Asp Gln
145 150 155 160

Asp Pro Val Val Val Glu Phe Asn Val Ser Ala Ile Glu Met Pro Val
165 170 175

Val Tyr Asn Lys Gln Gly Trp His Asp Pro Lys Ala Arg Phe Tyr Val
180 185 190

Met Asp Glu Asp Leu Asp Asp Ile Leu Ser Gly Lys Lys Glu Pro Glu
195 200 205

Pro Leu Val Phe His Val Pro Ala Gly Thr Cys Ile Arg Met Asn Tyr
210 215 220

Thr Asn Arg Met Pro His Ile Leu Asp Gly Asp Ala Phe Gln Leu Val
225 230 235 240

Thr Arg Thr Tyr Glu Asn Gly Phe His Ile His Phe Val Lys Phe Asp
245 250 255

-continued

```
Val Leu Ala Cys Asp Gly Gly Asn Val Gly Trp Asn Tyr Asp Ser Ala
            260                 265                 270

Val Leu Pro Gly Gln Thr Ile Arg Tyr Glu Trp Tyr Ala Glu Thr Glu
        275                 280                 285

Leu Lys Ala Trp Phe Phe His Asp His Leu Phe
    290                 295


<210> SEQ ID NO 8
<211> LENGTH: 38
<212> TYPE: DNA
<213> ORGANISM: Artificial Sequence
<220> FEATURE:
<223> OTHER INFORMATION: PCR forward primer

<400> SEQUENCE: 8

ccgcggtatg cgtcattcgg attatttgaa aaatttgt                              38


<210> SEQ ID NO 9
<211> LENGTH: 29
<212> TYPE: DNA
<213> ORGANISM: Artificial Sequence
<220> FEATURE:
<223> OTHER INFORMATION: PCR reverse primer

<400> SEQUENCE: 9

gtcgactgcc ttttcttcat tgtcccacc                                        29


<210> SEQ ID NO 10
<211> LENGTH: 19
<212> TYPE: PRT
<213> ORGANISM: Artificial Sequence
<220> FEATURE:
<223> OTHER INFORMATION: Linker

<400> SEQUENCE: 10

Val Asp Leu Gln Gly Asp His Gly Leu Ser Ala Trp Ser His Pro Gln
1               5                   10                  15

Phe Glu Lys
```

RECOMBINANT MANGANESE OXIDASE

FIELD

In general, the field is recombinantly produced bacterial enzymes. More specifically, the field is recombinantly produced manganese oxidase enzymes from *Bacillus* species.

BACKGROUND

Reactive $MnO_2$ oxides are ubiquitous in the environment, and control the bioavailability and distribution of many toxic and essential elements and organic compounds (Ulrich H J & Stone A T, *Environmental Science and Technology* 23, 421-428 (1989); Stone A T and Morgan J J, *Environmental Science and Technology* 18, 450-456 (1984) Stone A T and Morgan J J, *Environmental Science and Technology* 18, 617-624 (1984) and Tebo B M et al, *Annual Review of Earth and Planetary Sciences* 32, 287-328 (2004) all of which are incorporated by reference herein). Their formation is thought to be dependent on microbial enzymes, because spontaneous Mn(II) to Mn(IV) oxidation is slow (Hastings D & Emerson S, *Geochimica et Cosmochimica Acta* 50, 1819-1824 (1986); incorporated by reference herein).

Mn(IV) oxides are recognized as playing an important role in global biogeochemical cycles by linking Mn cycling with other elemental cycles such as S, C, N, P, trace elements and radionuclides through scavenging and oxidation reactions. In the environment, microorganisms are believed to have major control of the formation of Mn oxide minerals. Multicopper oxidases have been implicated as the Mn oxidase in several model Mn-oxidizing bacteria including *Leptothrix* species, *Pseudomonas putida, Pedomicrobium* species and diverse marine spore forming *Bacillus* species whose spores are capable of oxidizing Mn(II) (Corstjens PLAM et al, *Geomicroscopy J* 14, 91-108 (2009); Geszvain K et al, *Applied and Environmental Microbiology* 79, 357-366 (2013); Ridge J P et al, *Environmental Microbiology* 9, 944-953 (2007); Lee Y, *Oxidation of Cobalt: Characterization and its Significance in Marine Environments* p 159, University of California, San Diego (1994); and Francis C A and Tebo B M *Appl and Environmental Microbiology* 68, 874-880 (2002); all of which are incorporated by reference herein.)

Several species of marine *Bacillus* spores oxidize Mn(II) on their exosporium, the outermost layer of the spore, encrusting them with Mn(IV) oxides (Hastings & Emerson, 1986 supra; Francis C A et al, *Archives of Microbiology* 178, 450-456 (2002); Dick G J et al, *Applied and Environmental Microbiology* 72, 3184-3190 (2006); Morgan J J, *Metal Ions in Biological Systems* 37, 1-34 (2000); Nealson K H et al, *Adv Appl Microbiol* 33, 279-318 (1988); Tebo B M et al, *Reviews in Minerology* 35, 259-266 (1997); and Bargar J R et al, *Geochimica et Cosmochimica Acta* 64, 2775-2778 (2000); all of which are incorporated by reference herein.) Molecular studies have identified the mnx (Mn oxidation) genes, including mnxG, a putative multicopper oxidase (MCO), as responsible for this two-electron oxidation (Francis et al, 2002 supra; Van Waasbergen L G et al, *Journal of Bacteriology* 175, 7594-7603 (1993); van Waasbergen et al, *Journal of Bacteriology* 178, 3517-3530 (1996); and Dick G J et al, *Appl Environ Microbiol* 74, 1527-1534 (2008); all of which are incorporated by reference herein).

SUMMARY

Recombinant expression and purification of multicopper oxidases in quantities sufficient for biochemical characterization and industrial applicability has not been described prior to this disclosure. Further, it is described herein for the first time that a multicopper oxidase catalyzes a two-electron oxidation of Mn(II) to form Mn(IV) oxide.

Disclosed herein is the expression and purification of an active recombinant Mn oxidase complex that comprises the expression of at least three genes in the mnx operon of *Bacillus*. Purification of an active recombinant Mn oxidase complex from the mnxDEFG expression construct results in the formation of a blue (Abs max 590 nm) complex comprising MnxE, MnxF, and MnxG proteins. Also disclosed are recombinant bacterial expression vectors that may be used to express the manganese oxidase complex, methods of expressing and purifying the recombinant manganese oxidase complex, and methods of synthesizing $MnO_2$ using the recombinant manganese oxidase complex.

The manganese oxidase complex facilitates both electron transfers from Mn(II) to Mn(III) and from Mn(III) to Mn(IV). X-ray absorption spectroscopy of the Mn mineral product confirmed its similarity to Mn(IV) oxides generated by whole spores. Mn oxidation from soluble Mn(II) to Mn(IV) oxides is a two step reaction catalyzed by a complex comprising a multicopper oxidase.

BRIEF DESCRIPTION OF THE DRAWINGS

Some of the drawings in this disclosure are images that may not reproduce properly in a patent application publication. Additionally, some of the graphs, plots, and photographic images may be better understood using color, which is not available in a patent application publication. Applicants consider all originally disclosed images and graphs (whether in color or not) part of the original disclosure and reserve the right to present high quality and/or color images of the herein described figures in later proceedings.

Figure 8A:
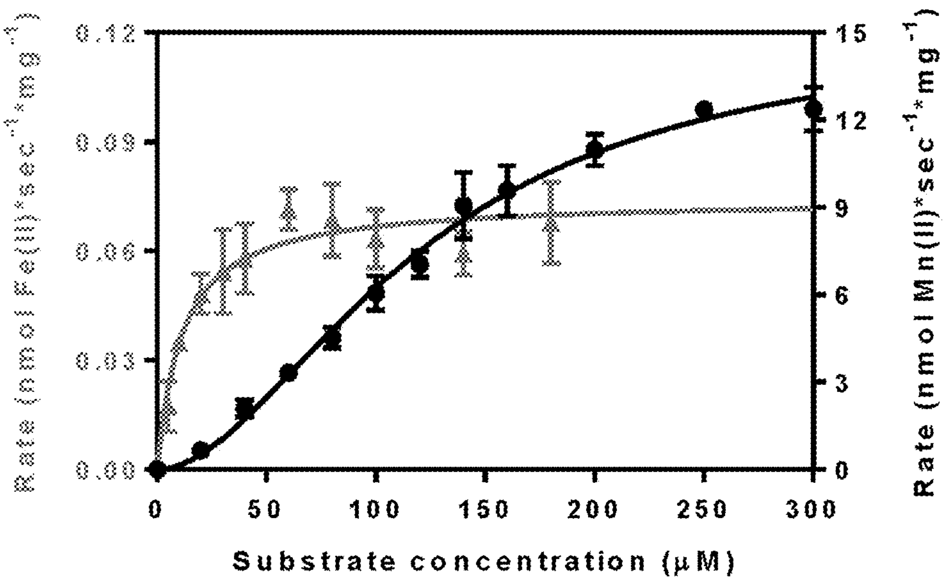
FIG. 8A is a plot showing the initial oxidation velocities of Fe(II) (triangles), and Mn(II) (circles) plotted against initial substrate concentration in a reaction catalyzed by the recombinant Mn oxidase complex. Fe(II) and Mn(II) oxidation by the recombinant Mn oxidase complex is followed by quenching the reaction with FerroZine (abs max 570 nm) and leucoberbelin blue (abs max 618 nm), respectively.
Figure 8B:
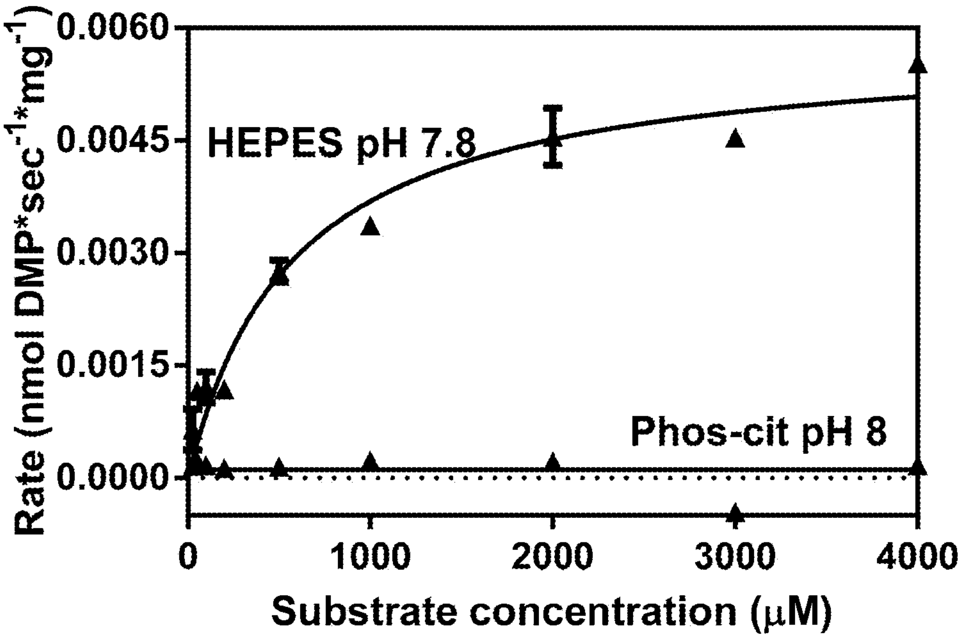
FIG. 8B is a plot showing the initial oxidation velocity of DMP plotted against initial substrate concentration in a reaction catalyzed by the recombinant Mn oxidase complex. DMP oxidation in HEPES is directly followed by the change in absorbance at 468 nm $\epsilon$=49.6 $mM^{-1}$ $cm^{-1}$
Figure 8C:
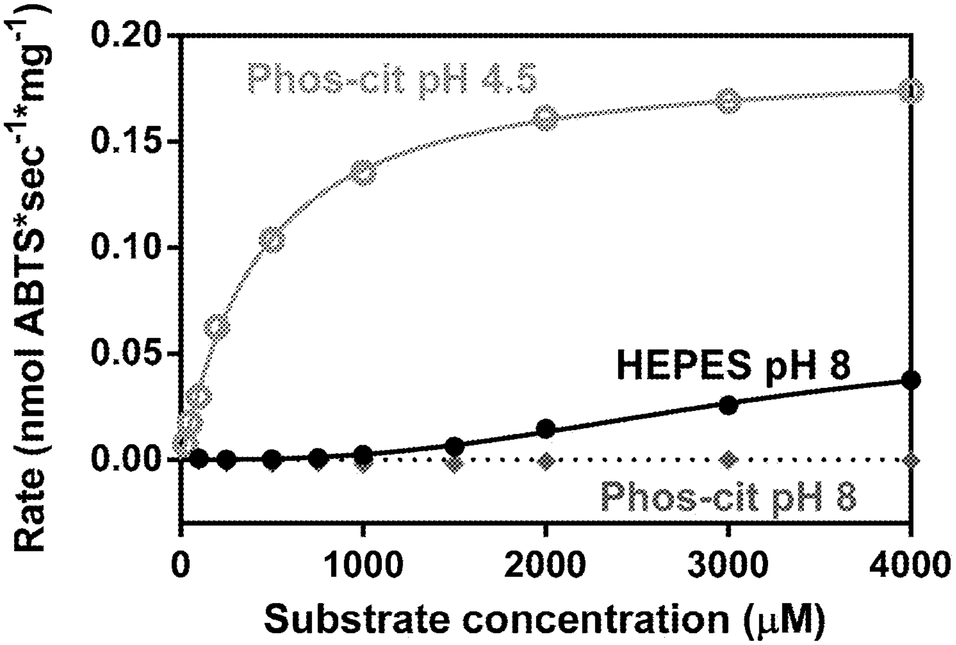
FIG. 8C is a plot showing the initial oxidation velocity of ABTS plotted against initial substrate concentration in a reaction catalyzed by the recombinant Mn oxidase complex. ABTS oxidation in phosphate-citrate buffer_is directly followed by the change in absorbance at and 420 nm $\epsilon$=36 $mM^{-1}$ $cm^{-1}$.

All plots in FIGS. 8A, 8B, and 8C were fitted with either Michaelis-Menten or allosteric sigmoidal functions as appropriate.

SEQUENCE LISTING

SEQ ID NO: 1 is a nucleic acid sequence of the *Bacillus* sp strain PL-12 Mnx operon that was cloned into a pTBX1 vector described in Example 1 below.

SEQ ID NO: 2 is a sequence of a forward primer used to amplify and clone SEQ ID NO: 1

SEQ ID NO: 3 is a sequence of a reverse primer used to amplify and clone SEQ ID NO: 1

SEQ ID NO: 4 is an amino acid sequence of MnxD

SEQ ID NO: 5 is an amino acid sequence of MnxE

SEQ ID NO: 6 is an amino acid sequence of MnxF

SEQ ID NO: 7 is an amino acid sequence of MnxG.

SEQ ID NO: 8 is a sequence of a second forward primer used to amplify and clone the Mnx operon (SEQ ID NO: 1).

SEQ ID NO: 9 is a sequence of a second reverse primer used to amplify and clone the Mnx operon (SEQ ID NO: 1).

SEQ ID NO: 10 is a tag sequence that can be used in the purification of the recombinant Mn oxidase complex.

DETAILED DESCRIPTION

Terms

Unless otherwise noted, technical terms are used according to conventional usage. Definitions of common terms in molecular biology may be found in Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCR Publishers, Inc., 1995 (ISBN 1-56081-569-8).

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes."

In addition, the materials, methods, and examples are illustrative only and not intended to be limiting. In order to facilitate review of the various embodiments of the disclosure, the following explanations of specific terms are provided:

Conservative Variants:

A substitution of an amino acid residue for another amino acid residue having similar biochemical properties. "Conservative" amino acid substitutions are those substitutions that do not substantially affect or decrease an activity of an MHC Class II polypeptide, such as an MHC class II al polypeptide. A polypeptide can include one or more amino acid substitutions, for example 1-10 conservative substitutions, 2-5 conservative substitutions, 4-9 conservative substitutions, such as 1, 2, 5 or 10 conservative substitutions. Specific, non-limiting examples of a conservative substitution include the following examples:

| Original Amino Acid | Conservative Substitutions |
|---|---|
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |

-continued

| Original Amino Acid | Conservative Substitutions |
|---|---|
| Thr | Ser |
| Trp | Tyr |
| Tyr | Trp; Phe |
| Val | Ile; Leu |

Contacting:

Placement in direct physical association, including contacting of a solid with a solid, a liquid with a liquid, a liquid with a solid, or either a liquid or a solid with a cell or tissue, whether in vitro or in vivo. Contacting can occur in vitro with isolated cells or tissue or in vivo by administering to a subject.

Isolated:

An "isolated" biological component (such as a nucleic acid, peptide or protein) has been substantially separated, produced apart from, or purified away from other biological components in the cell of the organism in which the component occurs, e.g., other chromosomal and extrachromosomal DNA and RNA, and proteins. Nucleic acids, peptides and proteins which have been "isolated" thus include nucleic acids and proteins purified by standard purification methods. The term also embraces nucleic acids, peptides and proteins prepared by recombinant expression in a host cell, as well as chemically synthesized nucleic acids.

Operably Linked:

A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame. In some examples, a promoter sequence is operably linked to a protein encoding sequence, such that the promoter drives transcription of the linked nucleic acid and/or expression of the protein.

Promoter:

Promoters are sequences of DNA near the 5' end of a gene that act as a binding site for RNA polymerase, and from which transcription is initiated. A promoter includes necessary nucleic acid sequences near the start site of transcription, such as, in the case of a polymerase II type promoter, a TATA element. In one embodiment, a promoter includes an enhancer. In another embodiment, a promoter includes a repressor element.

Promoters can be constitutively active, such as a promoter that is continuously active and is not subject to regulation by external signals or molecules. In some examples, a constitutive promoter is active such that expression of a sequence operably linked to the promoter is expressed ubiquitously (for example, in all cells of a tissue or in all cells of an organism and/or at all times in a single cell or organism, without regard to temporal or developmental stage).

An inducible promoter is a promoter that has activity that is increased (or that is de-repressed) by some change in the environment of the cell such as the addition of a particular agent to the cell media or a removal of a nutrient or other component from the media of the cell.

Polypeptide:

A polymer in which the monomers are amino acid residues which are joined together through amide bonds. When the amino acids are alpha-amino acids, either the L-optical isomer or the D-optical isomer can be used, the L-isomers being preferred. The terms "polypeptide" or "protein" or "peptide" as used herein are intended to encompass any amino acid sequence and include modified sequences such as glycoproteins. The term "polypeptide" or "protein" or "peptide" is specifically intended to cover naturally occurring proteins, as well as those which are recombinantly or synthetically produced. It should be noted that the term "polypeptide" or "protein" includes naturally occurring modified forms of the proteins, such as glycosylated, phosphorylated, or ubiquinated forms.

Purified:

The term purified does not require absolute purity; rather, it is intended as a relative term. Thus, for example, a purified peptide preparation is one in which the peptide or protein is more enriched than the peptide or protein is in its environment, for example within a cell or in a preparation. Preferably, a preparation is purified such that the protein or peptide represents at least 50% of the total peptide or protein content of the preparation. In some embodiments, a purified preparation contains at least 60%, at least 70%, at least 80%, at least 85%, at least 90%, at least 95% or more of the protein or peptide.

Recombinant:

A recombinant nucleic acid or polypeptide is one that has a sequence that is not naturally occurring or has a sequence that is made by an artificial combination of two or more otherwise separated segments of sequence. This artificial combination is often accomplished by chemical synthesis or, more commonly, by the artificial manipulation of isolated segments of nucleic acids, e.g., by genetic engineering techniques. A recombinant polypeptide can also refer to a polypeptide that has been made using recombinant nucleic acids, including recombinant nucleic acids transferred to a host organism that is not the natural source of the polypeptide (for example, nucleic acids encoding polypeptides that form a *Bacillus* Mn oxidase complex can be transferred to *E. coli* and expressed).

Sequence Identity/Similarity/Homology:

The identity/homology between two nucleic acid sequences, or two amino acid sequences, is expressed in terms of the similarity between the sequences, otherwise referred to as sequence identity. Sequence identity is frequently measured in terms of percentage identity (or homology, the terms are interchangable); the higher the percentage, the more homologous the two sequences are.

Methods of alignment of sequences for comparison are well known in the art. Various programs and alignment algorithms are described in: Smith & Waterman, Adv. Appl. Math. 2: 482, 1981; Needleman & Wunsch, J. Mol. Biol. 48: 443, 1970; Pearson & Lipman, Proc. Natl. Acad. Sci. USA 85: 2444, 1988; Higgins & Sharp, Gene, 73: 237-244, 1988; Higgins & Sharp, Comput. Appl. Biosci. 5: 151-153, 1989; Corpet et al., Nucl. Acids Res. 16, 10881-10890, 1988; Huang et al., Comput. Appl. Biosci. 8, 155-165, 1992; and Pearson, Methods Mol. Biol. 24:307-331, 1994. Altschul et al. (J. Mol. Biol. 215:403-410, 1990) presents a detailed consideration of sequence alignment methods and homology calculations. The NCBI Basic Local Alignment Search Tool (BLAST) (Altschul et al., J. Mol. Biol. 215:403-410, 1990) is available from several sources, including the National Center for Biotechnology Information (NCBI, Bethesda, Md.) and on the Internet, for use in connection with the sequence analysis programs blastp, blastn, blastx, tblastn and tblastx. BLASTN is used to compare nucleic acid sequences, while BLASTP is used to compare amino acid sequences. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a nucleic acid sequence that has 1166 matches when aligned with a test sequence having 1154 nucleotides is 75.0 percent identical to the test sequence (1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer. In another example, a target sequence containing a 20-25 nucleotide region that aligns with 20 consecutive nucleotides from an identified sequence as follows contains a region that shares 75 percent sequence identity to that identified sequence (that is, 15÷20*100=75).

For comparisons of amino acid sequences of greater than about 30 amino acids, the Blast 2 sequences function is employed using the default BLOSUM62 matrix set to default parameters, (gap existence cost of 11, and a per residue gap cost 5 of 1). Homologs are typically characterized by possession of at least 70% sequence identity counted over the full-length 5 alignment with an amino acid sequence using the NCBI Basic Blast 2.0, gapped blastp with databases such as the nr or swissprot database. Queries searched with the blastn program are filtered with DUST (Hancock and Armstrong, 1994, Comput. Appl. Biosci. 10:67-70). Other programs use SEG. In addition, a manual alignment can be performed. Proteins with even greater similarity will show increasing percentage identities when assessed by this method, such as at least about 75%, 80%, 85%, 90%, 95%, 98%, or 99% sequence identity to a protein.

One indication that two nucleic acid molecules are closely related is that the two molecules hybridize to each other under stringent conditions, as described above. Nucleic acid sequences that do not show a high degree of identity may nevertheless encode identical or similar (conserved) amino acid sequences, due to the degeneracy of the genetic code. Changes in a nucleic acid sequence can be made using this degeneracy to produce multiple nucleic acid molecules that all encode substantially the same protein. An alternative (and not necessarily cumulative) indication that two nucleic acid sequences are substantially identical is that the polypeptide which the first nucleic acid encodes is immunologically cross reactive with the polypeptide encoded by the second nucleic acid.

Nucleic acid sequences that do not show a high degree of sequence identity may nevertheless encode similar amino acid sequences, due to the degeneracy of the genetic code. It is understood that changes in nucleic acid sequence can be made using this degeneracy to produce multiple nucleic acid molecules that all encode substantially the same protein.

One of skill in the art will appreciate that the particular sequence identity ranges are provided for guidance only; it is possible that strongly significant homologs could be obtained that fall outside the ranges provided particularly if those homologs have a similar or identical function and a similar or identical level of activity to one another.

Manganese Oxidase Complexes

A manganese oxidase complex can be any combination of one or more polypeptides bound by covalent or non-covalent interactions that catalyzes the oxidation reaction of Mn(II)→Mn(IV). This includes polypeptide complexes that catalyze the oxidation reactions Mn(II)→Mn(III)→Mn(IV) or polypeptide complexes that catalyze the reaction Mn(II)→Mn(IV)→$MnO_2$. An example of a manganese oxidase complex is a complex comprising MnxG (SEQ ID NO: 7), MnxE (SEQ ID NO: 5) and MnxF (SEQ ID NO: 6). The complex may optionally comprise MnxD (SEQ ID NO: 4).

Disclosed herein is a recombinantly produced *Bacillus* sp. manganese oxidase complex comprising MnxG (SEQ ID NO: 7), MnxE (SEQ ID NO: 5), and MnxF (SEQ ID NO: 6). The recombinant Mn oxidase complex can also comprise MnxD (SEQ ID NO: 4). Also disclosed herein is a bacterial expression vector that can be used in the expression of the recombinant manganese oxidase complex, an *E. coli* bacterium comprising the bacterial expression vector and a method of expressing and purifying a recombinant *Bacillus* sp. Mn oxidase complex.

The manganese oxidase complex can be derived from any *Bacillus* or other bacterial species that expresses MnxG, MnxE, MnxF, or any homolog thereof that may be identified by sequence homology or sequence identity to SEQ ID NO: 5, SEQ ID NO: 6, or SEQ ID NO: 7 described herein or that catalyze the same reaction at the same or a similar activity. These include homologs with 50% identity to, 60% identity to, 70% identity to, 80% identity to, 90% identity to, 95% identity to, 98% identity to, and 99% identity to any of MnxG, MnxE, MnxF, or MnxD. Such homologs include MnxG, MnxE, and MnxF from *Bacillus* strains PL-12, MB-7, SG-1, GB02-31, GB02-27, GB02-21B, GB02-14C, GB02-8B, GB02-30, GB02-25, GB02-16, GB02-12, GB02-2A, PL-7, PL-26, PL-16, MB-5, MB-1, MB-11, SD-18, PL-30, PL-21, MB-3, MB-12, MK3-1, HM06-02, *Clostridium perfringens, Stigmatella aurantiaca*, or *Ornithinibacillus californiensis*. One of skill in the art in light of this disclosure would be able to identify, synthesize and purify MnxG, MnxE, MnxF, or MnxD homologs from any bacterium including any *Bacillus* species, or strain capable of oxidizing manganese, including those listed above.

A bacterial expression vector can be any polynucleotide sequence that comprises a set of nucleic acid sequences that can be translated into a protein within a bacterium such as an *E. coli* bacterium. Expression vectors may include one or more sequences that cause expression such as promoters and enhancers. Expression vectors may also include other sequences such as selection markers including antibiotic and other resistance markers.

One example of an inducible promoter that may be used in a bacterial expression system is the T7 promoter which induces expression by infecting the bacterial cells with bacteriophage T7 or by the addition of IPTG to the growth media of the bacterial cells. Other inducible promoters that may be used in bacterial expression systems include the β-lactamase promoter, the phage lambda PL and PR promoters, the *E. coli* galactose promoter, arabinose promoter, alkaline phosphatase promoter, trp promoter, lactose operon promoter or any other inducible promoter known in the art.

In some examples, a polypeptide such as a recombinant Mn oxidase complex or any component thereof may comprise a label. A label may be any substance capable of aiding a machine, detector, sensor, device, column, or enhanced or unenhanced human eye from differentiating a labeled composition from an unlabeled composition. Labels may be used for any of a number of purposes and one skilled in the art will understand how to match the proper label with the proper purpose. Examples of uses of labels include purification of biomolecules, identification of biomolecules, detection of the presence of biomolecules and localization of biomolecules within a cell, tissue, or organism. Examples of labels include but are not limited to: radioactive isotopes or chelates thereof; dyes (fluorescent or nonfluorescent); stains; enzymes; nonradioactive metals; magnets, such as magnetic beads; protein tags; any antibody epitope; biotin; any specific example of any of these; any combination of any of these; or any label now known or yet to be disclosed.

A label may be covalently attached to a biomolecule or bound through hydrogen bonding, Van Der Waals or other forces. A label may be associated with the N-terminus, the C-terminus or any amino acid in the case of a polypeptide or the 5' end, the 3' end or any nucleic acid residue in the case of a polynucleotide.

In some examples, the recombinant Mn oxidase complex is labeled with a protein tag. A protein tag comprises a sequence of one or more amino acids that may be used as a label as discussed above. In some examples, the protein tag is covalently bound to the polypeptide. It may be covalently bound to the N-terminal amino acid of the polypeptide, the C-terminal amino acid of the polypeptide or any other amino acid of the polypeptide. Often, the peptide tag is encoded by a polynucleotide sequence that is immediately 5' of a nucleic acid sequence coding for the polypeptide such that the protein tag is in the same reading frame as the nucleic acid sequence encoding the polypeptide. Protein tags may be used for all of the same purposes as labels listed above and are well known in the art. Examples of protein tags include chitin binding protein (CBP), maltose binding protein (MBP), glutathione-S-transferase (GST), poly-histidine (His), thioredoxin (TRX), FLAG, V5, c-Myc, HA-tag, green fluorescent protein (GFP) modified GFPs and GFP derivatives and other fluorescent proteins, such as EGFP, EBFP, YFP, BFP, CFP, ECFP and so forth. Other tags include a His-tag which facilitates purification on metal matrices. Other protein tags include BCCP, calmodulin, Nus, Thioredoxin, Streptavidin, SBP, and Ty, or any other combination of one or more amino acids that aids in the purification of biomolecules, the identification of biomolecules, the detection of the presence of biomolecules, or the localization of biomolecules within a cell, tissue, or organism.

EXAMPLES

The following examples are illustrative of disclosed methods. In light of this disclosure, those of skill in the art will recognize that variations of these examples and other examples of the disclosed method would be possible without undue experimentation.

Example 1—Expression and Purification of a Recombinant Mn Oxidase Complex

Enzymatic Mn oxidation on the *Bacillus* spore surface overturns the widely held perception that bacterial spores are inactive, dormant cells. In fact, the *Bacillus* exosporium is made up of a highly ordered matrix of proteins and sugars responsible for interacting with the environment and conferring pathogenesis (Kailas L et al, *Proc Natl Acad Sci USA* 108, 16014-16019 (2011); incorporated by reference herein). Many attempts have been made to purify the Mn-oxidizing exosporium protein from *Bacillus* spores, but the protein exists in low abundance on the exosporium and is difficult to solubilize. Exosporium preparation and extraction takes about two weeks and yields very little, impure protein (see, for example Francis C A et al, *Archives of Microbiology* 178, 450-456 (2002) and Dick G J et al, *Appl Environ Microbiol* 74, 1527-1534 (2008), both of which are incorporated by reference herein.) In contrast, the expression system disclosed herein produces about 2 mg of purified *Bacillus* sp. strain PL-12 Mn(II) oxidase per liter of *E. coli* culture in five days.

Direct molecular evidence of oxidation in the *Bacillus* exosporium has been previously demonstrated by the presence of MnxF and MnxG in an active SDS PAGE gel band. However, co-expressing these genes in *E. coli* did not produce active protein (Dick G J et al 2008 supra).

It is disclosed herein that active protein can be obtained when the mnxDEFG operon construct is expressed without a tag in *E. coli* by inducing at 17° C. and loading with 2 mM $CuSO_4$ under microaerobic conditions (mnxD can be omitted from the construct.) The expression of tagged recombinant Mn oxidase complex is also disclosed. After lysis, *E. coli* proteins were removed by trypsin proteolytic digestion, or by heat precipitation at 70° C. for 20 min. The heat stable and trypsin cleavage resistant Mn(II) oxidase was purified by a series of native chromatography steps: hydrophobic interaction, gel filtration, and ion exchange. Enzymatic Mn(II)-oxidizing activity was demonstrated by the formation of brown Mn(IV) oxides after the addition of $Mn(II)Cl_2$ to protein in solution or protein run on a non-denaturing SDS-PAGE gel. The presence of oxidized Mn was confirmed by a colorimetric assay in which Mn(III) and Mn(IV) react with leucoberbilin blue (LBB) to turn the solution blue (Abs 618 nm).

Figure 1:
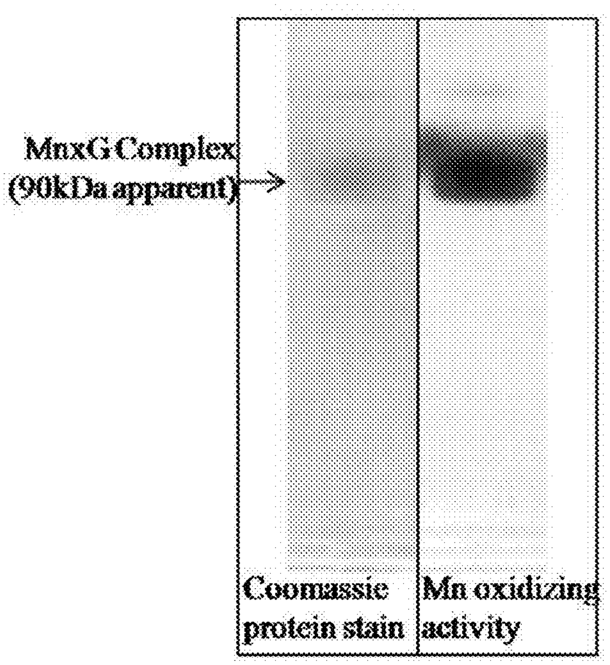
FIG. 1 is an image of an SDS PAGE gel of purified recombinant Mn oxidase complex diluted into Laemmli buffer and stained by Coomassie blue (lane 1) or incubated with Mn(II) (lane 2). The arrow indicates the native purified protein migrating to about the 90 kDa position of the molecular weight ladder.

To elucidate which mnxDEFG operon gene products were in the purified active complex, an in-gel Mn oxidation assay was performed as described in Francis C A & Tebo B M, Environmental Microbiology 68, 874-880 (2002); which is incorporated by reference herein. Non-denaturing SDS PAGE was used to select an active protein band for tandem mass spectrometry (MS/MS) identification (FIG. 1, left). MS/MS identified 100 unique peptides from MnxG, 10 from MnxE and 5 from MnxF. This is a surprising result because no multicopper oxidase had been previously purified as a multi-protein complex (Table 1). The molecular weight of the purified recombinant Mn oxidase complex determined by size exclusion chromatography, 230 kDa, suggests the presence of one MnxG (138 kDa) and an oligomer of 6-8 MnxE and MnxF subunits in total (12 kDa each), such as 3 MnxE and 3 MnxF subunits.

TABLE 1

Mnx peptides identified by tandem mass spectrometry, Peptide coverage is the percent of protein sequence covered by the peptides:

| ID | Mol Weight (kDa) | Unique peptides identified | Peptide coverage (%) |
|---|---|---|---|
| MnxG | 138 | 100 | 48.3 |
| MnxE | 12 | 10 | 48.2 |
| MnxF | 12 | 5 | 23.3 |

MnxE and MnxF have no conserved sequence homology to known proteins. However, a BLAST (Basic Local Alignment Search Tool) search indicated that MnxE, MnxF, and MnxG all have homologs in the spore-forming bacteria, *Cellulosilyticum lentocellum*, a cellulose degrading *Clostridium* species, and *Desulfotomaculum kuznetsovii*, a thermophilic methylotrophic sulfate-reducer. It is unknown if these organisms can oxidize Mn but because MnxE and MnxF are only conserved among spore-forming bacteria, they may be required for activity, stability, and/or localization of MnxG-like MCOs to the spore surface or exosporium.

The MnxG sequence predicts it to be a large, 6-domain multicopper oxidase, similar to human ceruloplasmin, a ferroxidase (Van Waasbergen L G et al, *J Bacteriol* 178, 3517-3530 (1996); incorporated by reference herein). Multicopper oxidases contain four copper atoms that couple the oxidation of phenolic or metal substrates to the sequential reduction of $O_2$ to $H_2O$. These four copper atoms reside in the blue Type 1 (Abs ~600 nm) center and the trinuclear center containing one Type 2 and two Type 3 (Abs ~330 nm) Cu atoms. In addition to these canonical Cu atoms, multicopper oxidases can also bind Cu in extra T1 sites and in labile regulatory sites (Lindley P F et al, *Biol Inorg Chem* 2, 454-463 (1997) and Roberts S A et al, *J Biol Chem* 278, 31958-31963 (2003); both of which are incorporated by reference herein). The purified recombinant Mn oxidase complex is blue colored (Abs 590 nm) (FIG. 1, right) and has a copper occupancy of 6.4±0.02 Cu per mol or higher depending on the number of MnxE and MnxF that make up the complex. Copper occupancy was determined by inductively coupled plasma-optical emission spectroscopy (ICP-OES) analysis.

Example 2—Metal Content of the Mnx Complex

Both the type I and type II Cu can also be observed by EPR in their oxidized states. In the past it has been difficult to determine the native state of Cu binding in MCOs because the stoichiometries were determined indirectly from EPR peak intensity, UV-vis 610/280 nm ratios, and amino acid sequence similarities (Musci G et al, *Archives of Biochemistry and Biophysics* 306, 111-118 (1993); incorporated by reference herein. These parameters change with respect to small variations in ligand-Cu coordination among the MCOs (Solomon El et al, *Chemical Reviews* 96, 2563-2605 (2004); incorporated by reference herein). Extra Cu binding beyond the canonical MCO center seems to be advantageous in various preparations throughout the literature. The recombinant Mn oxidase complex was expressed in excess Cu loading conditions to assist in solubility and complex formation but the purified recombinant Mn oxidase complex exhibited vastly different Cu binding stoichiometries depending on the buffer into which the recombinant Mn oxidase complex was dialyzed (Table 2).

TABLE 2

Metal content of recombinant Mn oxidase complex and Cu effect on Mn oxidation activity

| $MnxE_3F_3G$ | | Cu | | |
|---|---|---|---|---|
| (211 kDa) | | As purified | HEPES dialyzed | Tris dialyzed |
| M/protein | | 13.5 ± 2.69 | 15.1 ± 0.33 | 9.9 ± 0.99 |
| Mn(II) | $K_{0.5}$ (μM) | ND[a] | 123 ± 7.00 | 134.6 ± 9.16 |
| | $k_{cat}$ ($s^{-1}$) | ND | 16.1 ± 0.941 | 12.9 ± 0.758 |

Metal content per Mnx protein complex was determined by ICP OES. [a]ND not done.

To determine the metal content of the recombinant Mn oxidase protein complex (also abbreviated herein as Mnx), the purified protein was dialyzed in either 20 mM HEPES or Tris and 50 mM NaCl buffer after purification in Cu-supplemented Tris buffers. HEPES dialysis results in a Cu:Mnx stoichiometry of 15:1 whereas Tris dialysis results in a Cu:Mnx stoichiometry of 10:1. Both results suggest that the recombinant Mn oxidase complex is binding many more Cu atoms than necessary to fill the four MCO active sites. This has been observed for other MCOs such as CueO and ceruloplasmin (Musci et al, 1993; supra and Roberts S A et al, *J Biol Chem* 278, 31958-31963 (2003); incorporated by reference herein).

Figure 6A:
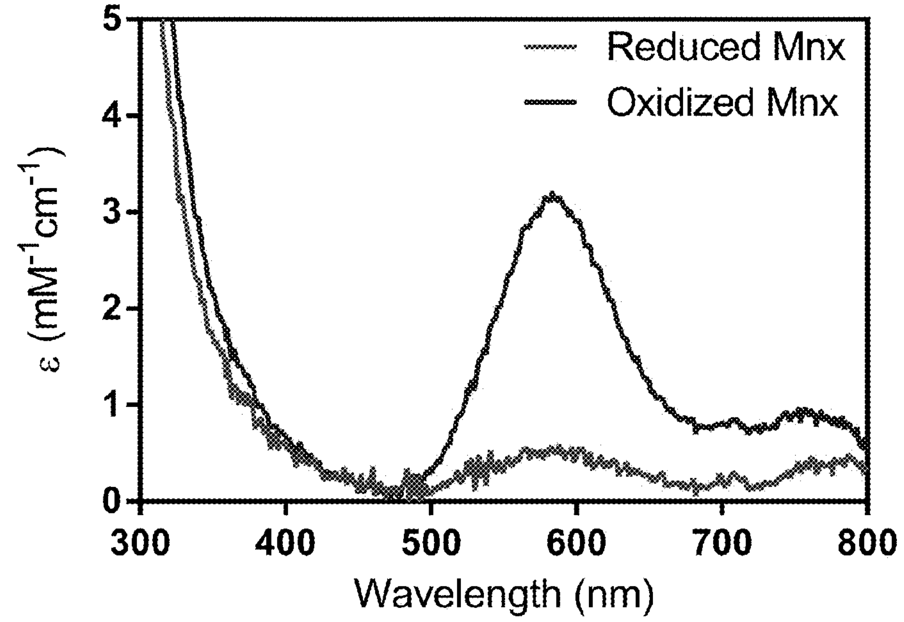
FIG. 6A is a plot of UV-visible spectra of a dithionite-reduced (red) and oxidized (blue) recombinant Mn oxidase complex. The blue type I Cu absorbance maximum at 590 nm is depleted in the reduced sample.
Figure 6B:
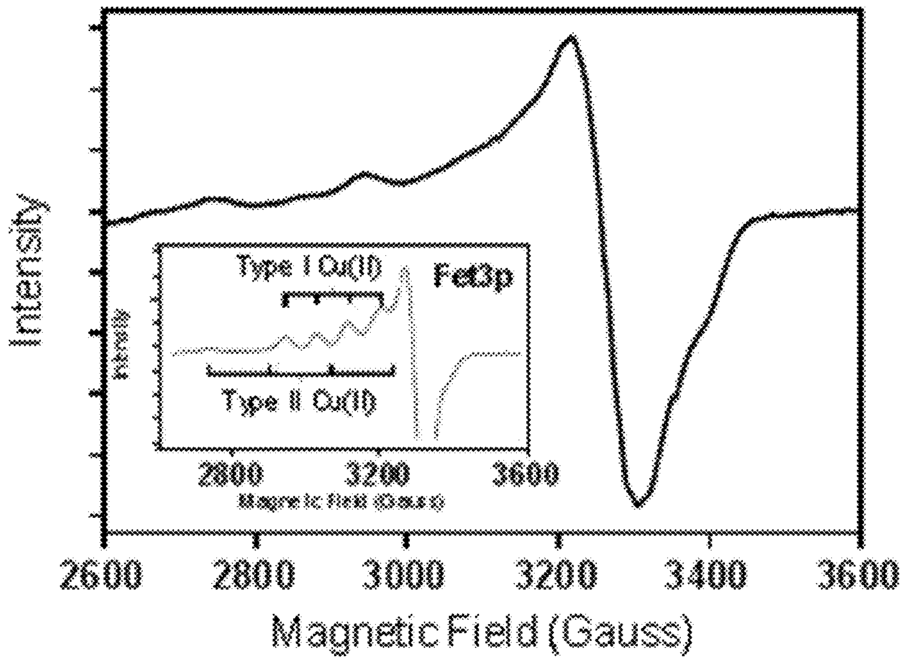
FIG. 6B is an EPR scan of the recombinant Mn oxidase complex that illuminates the typical trace of type I and type II Cu described in *S. cerevisiae* Fet3p (inset) (Hassett R F et al, *J Biol Chem* 273, 23274-23282 (1998); incorporated by reference herein).

Coordination of Cu in the recombinant Mn oxidase complex was explored through UV-visible absorption and electron paramagnetic resonance (EPR) spectroscopies. The recombinant Mn oxidase complex has an indigo blue color with an absorbance maximum of 590 nm indicative of the Cys-S—Cu charge transfer found on Type I Cu sites (Solomon et al, 1996 supra). Upon exposure to the reductant dithionite, the protein lost its color and absorbance maximum, further supporting the conclusion that the recombinant Mn oxidase complex contains a Type I Cu site (FIG. 6A). The electron paramagnetic resonance spectrum obtained from the oxidized Mn oxidase complex indicates characteristic peaks for the type I Cu and type II Cu (FIG. 6B). The type Ill Cu is EPR silent because it is antiferromagnetically coupled but is usually detected as UV-vis peak at 330 nm. This peak was not observed, although the sequence similarity, oxygen dependence, and azide inhibition of Mn oxidation (Soldatova et al, 2012 supra) suggests that the recombinant Mn oxidase complex does contain type Ill Cu, thus completing the requisite set of Cu centers of an MCO.

Example 3—Mnx Complex Consumes $O_2$ During Mn Oxidation

Figure 7A:
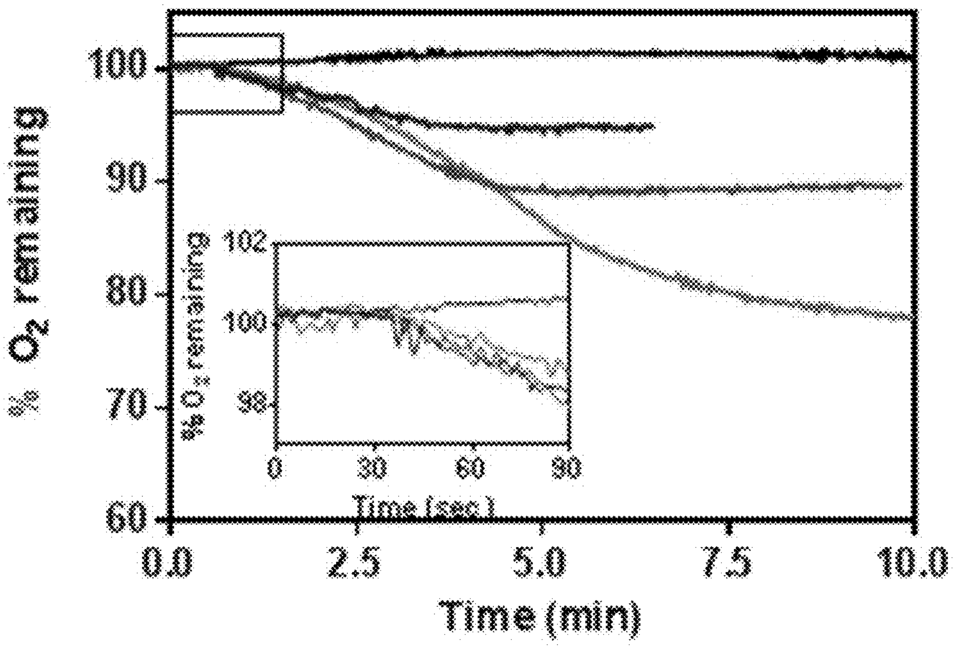
FIG. 7A is a plot showing representative runs of $O_2$ consumption by Mn oxidation with fully-loaded recombinant Mnx complex at varying concentrations of $MnCl_2$ added at t=0 (blue 50 μM, red 100 μM, green 200 μM, and black no enzyme). The inset focuses on the first 90 seconds of the reaction to highlight the consistent lag time of about 30 s in $O_2$ consumption.
Figure 7B:
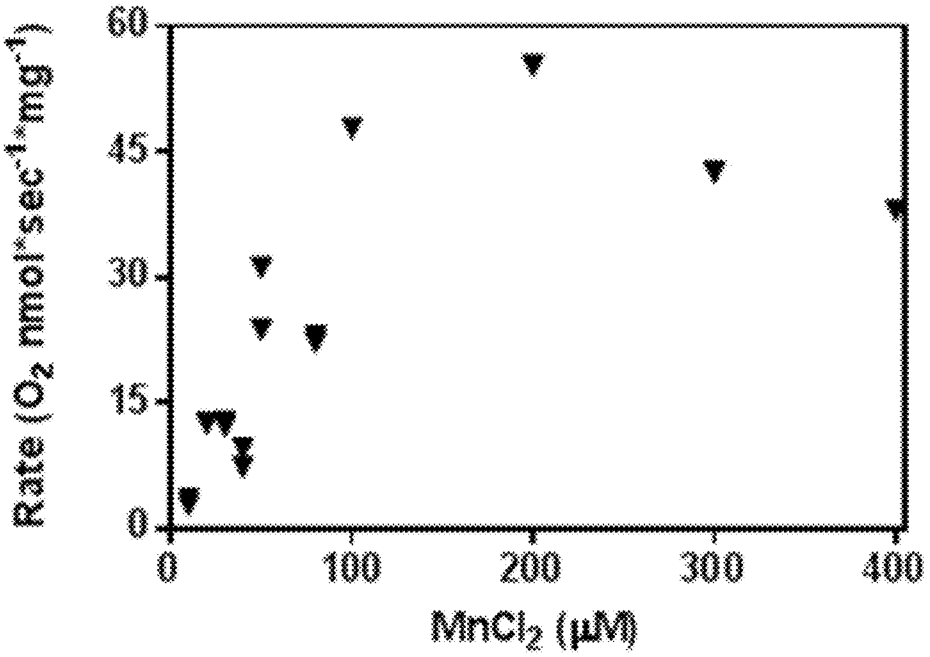
FIG. 7B is a plot of the Initial velocities of every run shown in FIG. 7A plotted against the starting Mn(II) concentration.
Figure 7C:
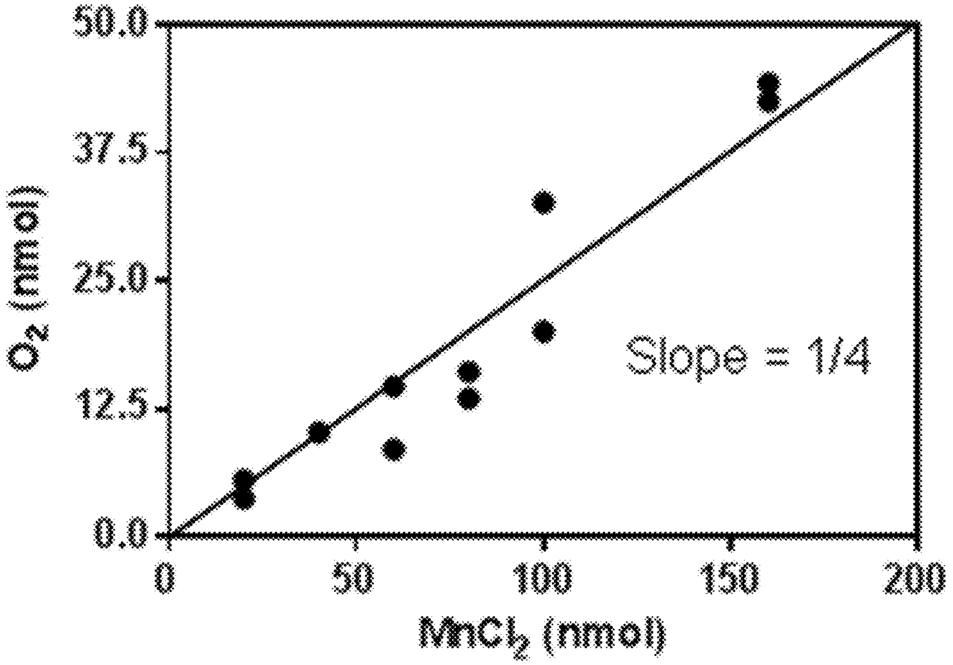
FIG. 7C is a plot of total $O_2$ consumed plotted against starting Mn(II) concentration and fit with linear regression, forced through the origin.

Also indicative of MCOs is the consumption of $O_2$ and its reduction to $H_2O$, terminating electron transfer at the trinuclear Cu center. $O_2$ consumption was measured on a Clark type electrode during Mn oxidation by the recombinant Mn oxidase complex. Following the addition of $MnCl_2$ to the enzyme, there is about a 30 s lag time before $O_2$ consumption is detected across all runs (FIG. 7A). Starting with a higher concentration of $MnCl_2$, results in a faster initial velocity of $O_2$ consumption (FIG. 7B). The plot of $MnCl_2$ added vs. $O_2$ consumed reveals a linear trend with a slope of about 0.252±0.0149. This indicates that for every 4 μmol Mn added 1 μmol $O_2$ is consumed (FIG. 7C). This stoichiometry supports the MCO mechanism of the four electron reduction required to generate 2 mol $H_2O$ from 1 mol $O_2$.

The oxygen dependence of Mn oxidation presented here supports the MCO mechanism: four electrons from Mn oxidation reduce 1 mole $O_2$ to 2 moles $H_2O$. If $Mn^{2+}$ is the electron donor to the MCO and 4 $Mn^{3+}$ form for every $4Mn^{2+}$ added, then the second oxidation step is facilitated by hydroxy- and oxo-bridging.

Figure 3:
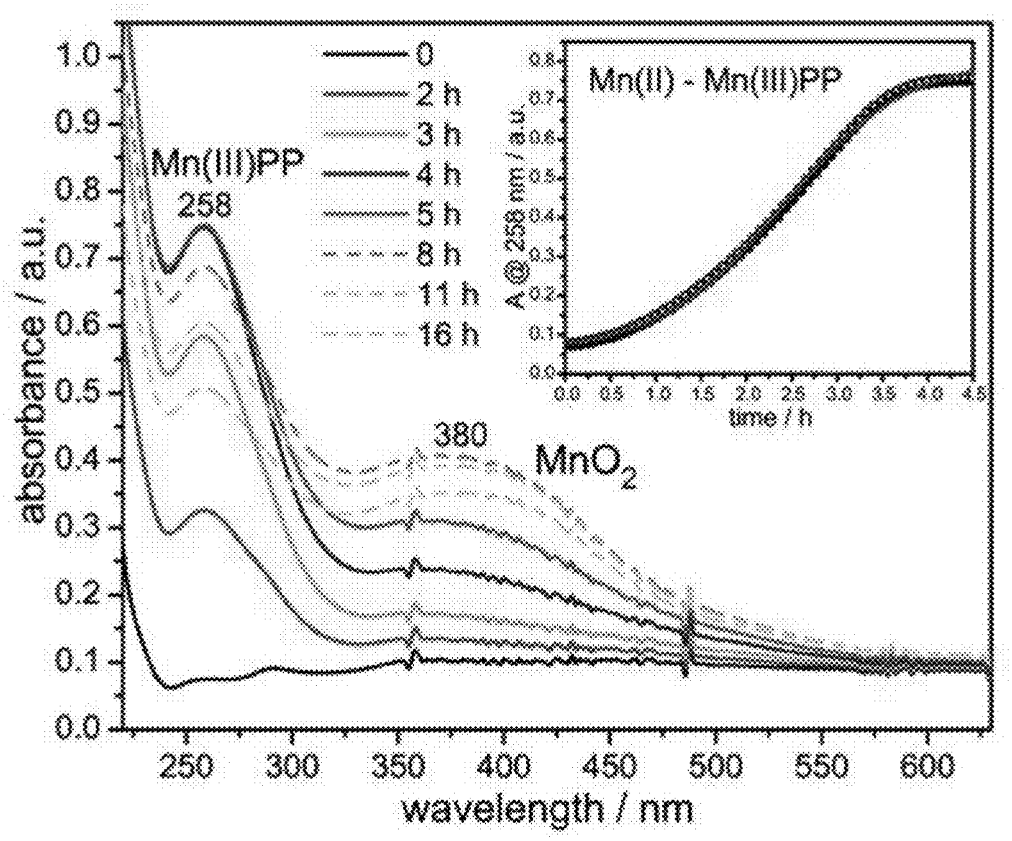
FIG. 3 is a graph of the absorption spectra of recombinant Mn oxidase complex in the presence of sodium pyrophosphate (PP), and $O_2$, after the addition of 0.1 mM $MnCl_2$ in HEPES buffer pH 7.5. The 258 nm absorption due to Mn(III)PP rises sigmoidally (inset).
Figure 4:
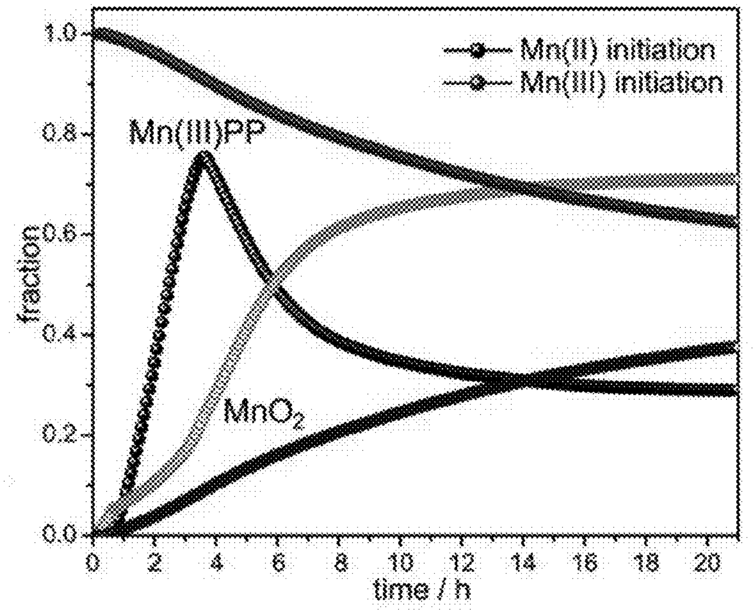
FIG. 4 is a graph of the absorption at 258 nm and 380 nm after addition of Mn(III)PP or $MnO_2$ to the recombinant Mn oxidase complex over time. Addition of 0.1 mM Mn(III) is followed by steady decay in the 258 nm and rise in the 360 nm absorption (obtained from component analysis of the spectra).

Example 4—Putative Mechanism of $MnO_2$ Formation by the Recombinant Mn Oxidase Complex To determine the course of $MnO_2$ formation catalyzed by the recombinant Mn oxidase complex, changes in the UV-vis absorption spectrum were monitored as Mn(II) or Mn(III) was allowed to react with oxygenated buffer in the presence of purified enzyme and the Mn(III) chelator, pyrophosphate (PP) (FIG. 3). When the reaction was initiated with Mn(II) a 258 nm peak, due to Mn(III)-PP, rises and then falls as a 360 nm peak, due to colloidal $MnO_2$. The initial time course of the rising Mn(III)-PP peak is sigmoidal, suggesting cooperative, allosteric substrate binding. When Mn(III)-PP initiates the reaction, the Mn(III)-PP peak decays as the $MnO_2$ forms (FIGS. 3 and 4). These results corroborate the earlier findings using *Bacillus* exosporium that Mn(II) oxidation to $MnO_2$ oxides is catalyzed by two single electron transfers (Soldatova A et al, (2013) infra; and Webb S M et al, *Proc Natl Acad Sci USA* 102, 5558-5563 (2005); both of which are incorporated by reference herein.)

Figure 2:
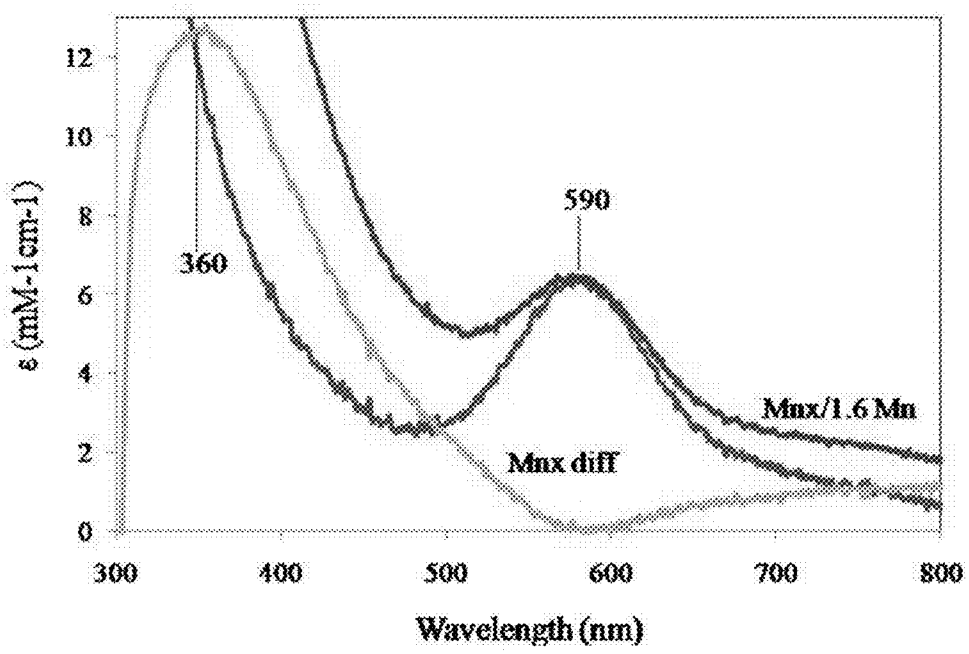
FIG. 2 is a UV-visible spectrum before (blue trace 590 nm band) and after incubation with 3-fold excess $MnCl_2$ and dialysis (red trace). The difference spectrum (green) shows Mn(IV) (360 nm band) bound to the recombinant Mn oxidase complex (1.6 Mn/mol protein).

Without being bound by theory, it could be hypothesized that a polynuclear mechanism, in which electron transfer from Mn(III) is driven by the formation of bridging oxides could be the mechanism of action of the recombinant Mn oxidase complex described herein. Consistent with this mechanism, it was observed that when three-fold excess Mn(II) was titrated with purified enzyme, dialyzed overnight, and concentrated, the solution displayed a 360 nm difference absorption band (FIG. 2) and LBB reactivity, suggestive of a polynuclear Mn(IV) species. ICP-OES analysis resulted in a stoichiometry of 1.6 moles Mn per mole of recombinant Mn oxidase complex. This suggests that Mn(II) oxidation results in a protein bound dinuclear or trinuclear Mn(IV) oxo complex that can nucleate $MnO_2$ formation.

Figure 5:
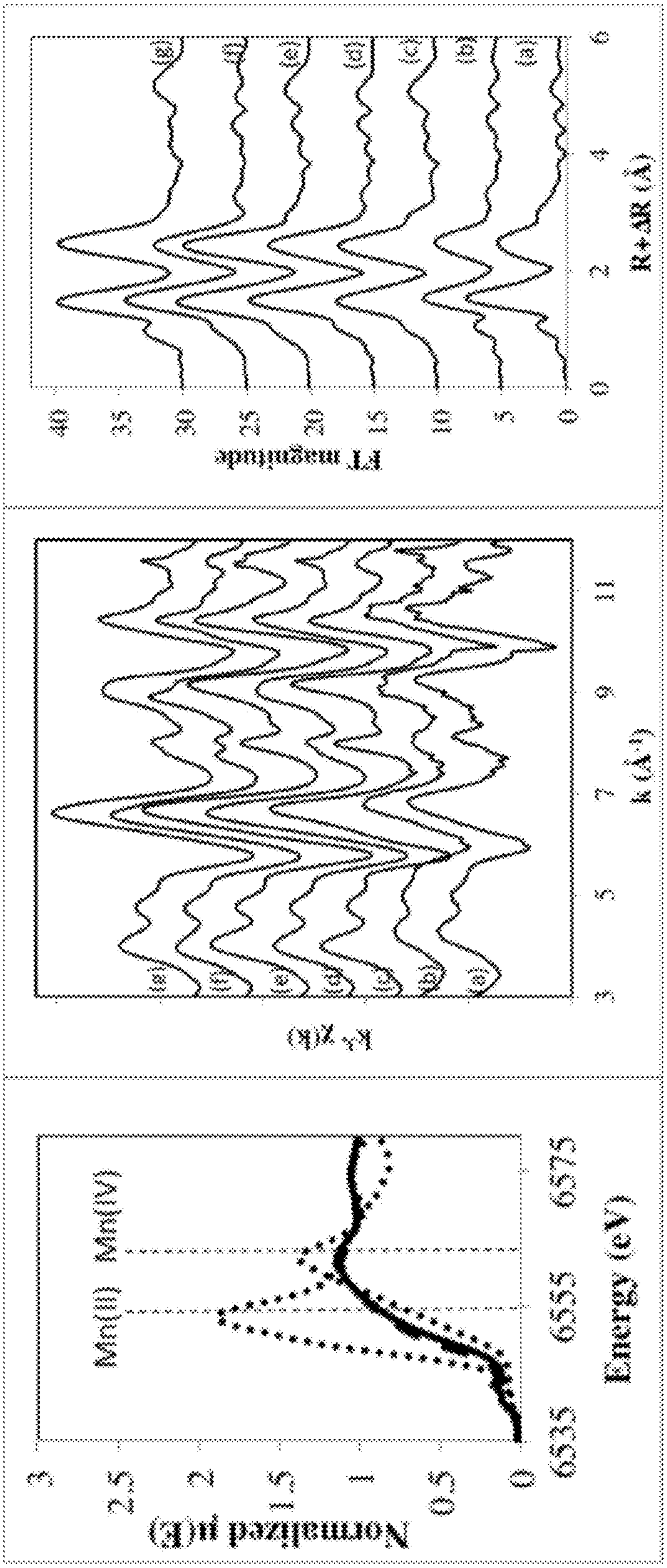
FIG. 5 is a set of three plots showing the Mn K-edge XANES (left), EXAFS (center) and Fourier transforms (right) of two different amounts of the recombinant Mn oxidase complex after incubation with Mn(II). Left: XANES spectra of 50 $\mu g \cdot L^{-1}$ (bold line) and 5 $\mu g \cdot L^{-1}$ (dashed line) recombinant Mn oxidase complex incubated in 100 $\mu M$ Mn(II). XANES of $MnCl_2.4H_2O$ and $\delta$-$MnO_2$ are provided as indicators for Mn(II) and Mn(IV) with maximum absorbance features at 6553 and 6562 eV, respectively. Mn K-edge EXAFS (center) and Fourier transforms (right) of the two different concentrations of the recombinant Mn oxidase complex. EXAFS of selected Mn oxides, produced by 50 μg·L-1 (a) or 5 μg·L-1 (b) of the recombinant Mn oxidase complex, biogenic Mn oxides formed by spores of *Bacillus* sp. SG-1 in NaCl solution (c), biogenic Mn oxides formed by spores of *Bacillus* sp. SG-1 in CaCl2 solution (d), δ-$MnO_2$ (e), triclinic birnessite (f), and hexagonal birnessite (g) are shown for comparison.

The Mn oxidation state and the structure of the $MnO_2$ made by the purified enzyme described herein were analyzed using X-ray absorption spectroscopy and compared to those previously reported for intact purified *Bacillus* sp. SG-1 spores (Bargar J R et al, *American Mineralogist* 90, 143-154 (2005); Webb S M et al, *Geomicrobiology J* 22, 181-193 (2005); Webb, S M et al, *American Mineralogist* 90, 1342-1357 (2005); all of which are incorporated by reference herein.) X-ray absorption near-edge spectra (XANES) of solid phases of two different concentrations of purified Mn oxidase complex, (5 and 50 $\mu g \cdot L^{-1}$) demonstrated that both preparations oxidized Mn(II) to Mn(IV) (FIG. 5). The absorbance maximum for these two preparations occurs near the white line of Mn(IV) at 6562 eV. Linear combination fitting of the data confirms a predominance of Mn(IV) in the samples with 20-30% Mn(II) and Mn(III) present, mostly as Mn(II) as evidenced by the shoulder at 6553 eV. Measurements of the Mn K-edge extended x-ray absorption fine structure (EXAFS) were also performed on these preparations (FIG. 5). It has been previously shown that Mn oxides formed by spores of *Bacillus* sp. SG-1 in NaCl solution were similar to δ-$MnO_2$, while in $CaCl_2$ solution biogenic Mn oxides exhibited features similar to triclinic or orthogonal manganates. Qualitatively, EXAFS of Mn oxides formed by purified Mn oxidase were similar to the spore product but with some differences between the Mn oxides depending on the amount of protein used. Specifically, EXAFS of Mn oxides formed with 50 $\mu g \cdot L^{-1}$ purified protein showed single antinodes at 8.0 and 9.3 Å-1 while Mn oxides produced from 5 $\mu g \cdot L^{-1}$ protein showed double antinodes (FIG. 5). Single antinodes can be found in hexagonal layer symmetry which includes δ-MnO2, hexagonal birnessites, and biogenic Mn oxides from *Bacillus* sp. SG-1 in NaCl, while double antinodes at 8.0 and 9.3 Å-1 can be observed in orthogonal layer symmetry such as triclinic birnessites and biogenic Mn oxides formed by spores of *Bacillus* sp. SG-1 in $CaCl_2$. Fourier transforms (FIG. 5 right) show that Mn oxides from purified Mn oxidase have most of the features observed in *Bacillus* sp. SG-1 spore generated Mn oxides in both NaCl and $CaCl_2$ solution (i.e., first peak (Mn—O) and second peak (edge-sharing Mn—Mn), and amplitude of multiple-scattering peak at 5.2 Å

Example 5—Recombinant Mn Oxidase Complex Oxidizes a Broad Range of Substrates Multicopper oxidases (MCOs) are known to have a broad substrate range including bulky phenolic compounds and transition metals Fe and Cu (Xiao and Wedd, *Australian J Chem* 64, 231-238 (2011); Reiss R et al, *PLoS ONE* 8 (6) 2013), both of which are incorporated by reference herein. Fine tuning substrate turnover over eons of evolution has given rise to a family of proteins that catalyze the oxidation of different substrates via the same mechanism. For example, it has been suggested that CueO in *E. coli* is tuned to Cu(I) oxidation so that it can detoxify excess Cu(I) to Cu(II) in the periplasm so it is easily exported (Outten F W et al, *J Biol Chem* 276, 30670-30677 (2001); incorporated by reference herein). Ceruloplasmin participates in metal homeostasis as well by oxidizing Fe(II) to regulate its concentration in the blood of mammals (Osaki S, *J Biol Chem* 24, 5053-5059 (1966) and Osaki S et al, *J Biol Chem* 241, 2746-2751 (1966); both of which are incorporated by reference herein). Laccases, such as CotA from *Bacillus subtilis* degrade plant lignin and other organics and synthesizes a brown pigment on the spore coat (Sakurai T and Kataoka K, *Chem Record* 7, 220-229 (2007); incorporated by reference herein). Determining the most efficient catalysis of the recombinant Mn oxidase complex at environmentally relevant conditions could point to a physiological function.

Unlike any other MCO, however is the capability of the recombinant Mn oxidase complex to directly catalyze both Mn(II) and Mn(III) oxidation, two energetically distinct reactions, to form reactive Mn(IV) oxides (Butterfield C N et al, *Proc Natl Acad Sci USA* 110, 11731-11735 (2013); incorporated by reference herein. From metals to large phenolics, multicopper oxidases have wide substrate specificities. Because the recombinant Mn oxidase complex is similar to the Fe oxidizing enzymes ceruloplasmin and Fet3p, the ability of the recombinant Mn oxidase complex to oxidize Fe was tested (FIG. 8A). The recombinant Mn oxidase complex has a high affinity to Fe (KM 9 μM) and oxidizes slower than Fet3p enzymes from yeast at pH 5 (Table 3) (Stoj et al., 2006 infra; Ziegler et al, 2011 infra). The recombinant Mn oxidase complex also readily oxidizes phenolic compounds. As described above, the *Bacillus* spore coat MCO, CotA, has also been reported to oxidize these compounds (Durão et al, 2008 infra; Koschorreck et al, 2008 infra). The activity of those MCOs was also compared to that of the recombinant Mn oxidase complex. The recombinant Mn oxidase complex oxidizes ABTS at pH 4.5 in a Phosphate-citrate buffer, but when the buffer system is switched to HEPES the recombinant Mn oxidase complex oxidizes ABTS at pH 8 (FIG. 8C). The recombinant Mn oxidase complex oxidizes 2,6-DMP at pH 8 in HEPES and is inactive in Phosphate-citrate buffer (FIG. 8B). In all cases, the recombinant Mn oxidase complex catalyzes both these reactions much slower than CotA does (Table 3).

TABLE 3

Mnx substrate activity compared to other MCOs
Activity with phenolic compounds, ABTS and 2,6-DMP, are compared between recombinant *Bacillus* PL-12 Mn oxidase complex and CotA enzymes from other *Bacillus* species. Date from the recombinant Mn oxidase complex are shown at pH 4.5 and pH 8.0 as indicated. Fe(II) oxidation activity is compared between the recombinant Mn oxidase complex and other six-domain ferroxidases from *Candida albicans* and *Saccharomyces cerevisiae*. *B. subtilis* CotA is described in Durão P et al, J Biol Inorg Chem 13, 183-193 (2008), incorporated by reference herein; *B. licheniformis* CotA is described in (Koschorreck K et al, *Appl Microbiol Biotech* 79, 217-224 (2008), incorporated by reference herein; *C. albicans* Fet3p is described in *Ziegler L* et al, *Mol Microbiol* 81, 473-485 (2011), incorporated by reference herein; and *S. cerevisiae* Fet3p is described in Stoj CS et al, *Biochemistry* 45, 12741-12749 (2006), incorporated by reference herein.

| Substrate | | Mnx *Bacillus* sp. PL-12 | | CotA *B. Subtilis* | CotA *B. licheniformis* |
|---|---|---|---|---|---|
| ABTS | $K_M$ (µM) | 456 ± 23.3 (pH 4.5) | 3126 ± 391 (pH 8) | 6.5 | 124 |
| | $k_{cat}$ ($s^{-1}$) | 0.206 ± 0.0136 (pH 4.5) | 0.0595 ± 0.00891 (pH 8) | 83 | 322 |
| 2,6-DMP | $K_M$ (µM) | 576 ± 163 | | 216 | 56.7 |
| | $k_{cat}$ ($s^{-1}$) | 0.00612 ± 4.98 × $10^{-4}$ | | 80 | 28 |
| | | | | Fet3p *C. albicans* | Fet3p *S. cerevisiae* |
| Fe(II) | $K_M$ (µM) | 9.00 ± 1.04 | | 7.9 ± 0.5 | 4.9 ± 0.8 |
| | $k_{cat}$ ($s^{-1}$) | 0.0744 ± 0.00779 | | 1.06 ± 0.02 | 0.835 ± 0.023 |

Not only does ABTS oxidation by the recombinant Mn oxidase complex have two pH optima, but also the kinetic traces differ from one another. At pH 4.5, the curve follows Michaelis-Menten kinetics while at pH 8, the curve fits the allosteric sigmoidal function much like Mn oxidation. DMP and Fe oxidation also have Michaelis-Menten kinetics trends. The $k_{cat}$ and maximum velocity increase from DMP<ABTS (pH 8)<ABTS (pH 4.5)<Fe<Mn (Table 2). The enzyme's substrate affinity increases thusly; ABTS (pH 8)<<DMP<ABTS (pH 4.5)<Mn<Fe.

The disclosed recombinant Mn oxidase complex oxidizes a wide variety of substrates but has by far the highest efficiency with Mn turnover, defining it as a metallo-oxidase with laccase-like activity. The recombinant Mn oxidase complex requires Cu to oxidize Mn while consuming oxygen at a pH optimum of 7.8, close to the marine environment from which the *Bacillus* strain from which the recombinant Mn oxidase complex was cloned was isolated (Francis C A and Tebo B M *Microbiology* 68, 874-880 (2002); incorporated by reference herein). Perhaps also not surprising is its ability to oxidize Fe at pH 5, similar to other metallo-oxidases (de Silva D et al, *J Biol Chem* 272, 14208-14213 (1997), incorporated by reference herein; and Kataoka et al, 2007 supra).

Example 6—Recombinant Mn Oxidase Complex Cloning and Purification Method 1

*Bacillus* sp. PL-12 genomic DNA was isolated with DNeasy kit (Qiagen). The mnxDEFG operon was amplified with Pfu Phusion high fidelity DNA polymerase (New England Biosciences) using forward primer 5'-GCTAGCATGCGTCATTCGGATTATTTGAAAAATTTGT-3' and reverse primer, 5'-CTCGAGTTATGCCTTTTCTTCATTGTCCCACCCC-3', including the mnxG stop codon. This amplicon was subcloned into pJet (Invitrogen) before insertion into pTXB1 (New England Biosciences) with NheI and XhoI (New England Biosciences). This yielded the pTXB1/mnxDEFG vector.

1 L LB was inoculated from 10 ml *E. coli* BL12(DE3) (pTXB1/mnxDEFG) with 100 µg/ml Ampicilin, 0.2 mM $CuSO_4$, and 10 mM Tris-HCl pH 7.5 added, grown until an OD ~0.5, chilled to 17° C., and induced with 0.1 mM IPTG for 18 hours (140 RPM). The shaking function was turned off for 22 hours with $CuSO_4$ added to 2 mM. The harvested cells were lysed into HIC start buffer supplemented with 10 mM CaCl, 1 mM CuSO4, and EDTA free protease inhibitor cocktail (Sigma) by two rounds of FRENCH press at 1000 psi. The crude extract was clarified by 20 minute incubation at 70° C. The recombinant Mn oxidase complex was purified by collecting active fractions of chromatography steps with 20 mM Tris-HCl supplemented with 50 µM CuSO4, Phenyl Sepharose 6 Fast Flow (high sub) from 1.25M NaCl to 0 NaCl in a stepwise gradient, HiPrep 16/60 Sephacryl S-300 High Resolution with 50 mM NaCl and 5% glucose added to prevent sticking to column, and HiTrap Q HP (GE Lifesciences) from 50 mM NaCl to 1 M NaCl in a linear gradient, where it was isolated from a single peak. Protein was quantified using the BCA (bicinchoninic acid) reagent (Thermo Scientific), using the size exclusion chromatography determined molecular weight of the purified complex of 230 kDa. Purified protein copper content was determined with a Perkin-Elmer Optima 2000 DV inductively coupled plasma optical emission spectrometer. UV-visible absorption spectrum was collected on Varion Cary 50 spectrophotometer.

Example 7—Mnx Complex Expression and Purification: Method 2 mnxD to mnxG were amplified from *Bacillus* sp. PL-12 genomic DNA by the following primers: Fwd 5'-CCGCGGTATGCGTCATTCGGATTATTTGAAAAATTTGT-3' and Rvs 5'-GTCGACTGCCTTTTCTTCATTGTCCCACC-3' and cloned by restriction enzyme digestion and ligation into the Strep-tag pASK/IBA3plus vector using SacII and SalI (sequences in bold). In place of the mnxG stop codon the Strep-tag (underlined) was engineered to a linker (italicized)

at the C-terminus of mnxG (VDLQGDHGLSA WSHPQFEK). The resulting construct was transformed into *E. coli* BL21 (DE3) and grown at 37° C. to an $OD_{600}$~0.5 in Luria-Bertani (LB) broth containing 0.2 mM CuSO4, 10 mM Tris-HCl pH 7.5, and 100 mg/L ampicillin. The temperature is then lowered to 17° C. by cooling the culture on ice or in a refrigerated shaker and then 0.2 mg/L anhydrotetracycline was added to induce transcription of the mnx genes. The cells continued to shake and express for 16-20 h. CuSO4 was added to a final concentration of 2 mM and the shaking function was stopped for at least 22 h more to allow for the microaerobic uptake of Cu ions into the *E. coli* cytoplasm as described in Durão et al, 2008 supra.

The cells were then harvested, suspended in Streptactin® equilibration buffer (100 mM Tris pH 8.0, 150 mM NaCl) amended with 10 mM CaCl2, 1 mM CuSO4, and an EDTA-Free SIGMAFAST™ Protease Inhibitor Cocktail Tablet, and lysed by sonication microtip for 1 min/ml cell lysate at 40% amplitude with 10 s on/off pulses on ice. The cell lysate was clarified by heat denaturation at 70° C. for 15 min. The cell debris was removed by centrifugation 15,000×g at 4° C. for 30 minutes and the supernatant was filtered through a 0.4 μm PVDF filter. The clarified lysate was then added to 5 ml column volume (CV) of Strep-Tactin Superflow Plus® (Qiagen) and slowly rotated for 1 hour at room temperature. By gravity flow, the unbound protein fraction was removed and the resin was washed with 20 CV Streptactin equilibration buffer. The recombinant Mn oxidase complex was eluted with 5 CV equilibration buffer plus 2.5 mM D-Desthiobiotin and the column was regenerated with 15 CV equilibration buffer plus 1 mM 2-(4-hydroxyphenylazo)benzoic acid. The eluted protein was concentrated to <1.5 ml on 100 kDa molecular weight cutoff filtration units (Millipore) for loading onto HiPrep® 16/60 Sephacryl S-200 High Resolution gel filtration column (GE Healthcare) equilibrated with 20 mM HEPES pH 7.8 50 mM NaCl 5% D-glucose (w/v) at 4° C. All buffers up to this point are supplemented with 50 μM CuSO4 to avoid Cu leaching by Tris. A single peak corresponding to a 230 kDa protein was collected, concentrated, and dialyzed three times for at least 3 h each at a volume of 1 L 20 mM HEPES pH 7.8, 50 mM NaCl for every 1 mL of protein sample at 4° C. The protein was quantified by the Thermo Scientific Pierce bicinchoninic acid (BCA) protein assay. It was then diluted with dialysis buffer to 0.2 mg/ml for kinetic studies or left concentrated for spectroscopy sample preparation, flash frozen in liquid nitrogen, and stored at −80° C.

Example 8—Other Methods

Mass Spec Analysis:

Purified protein was run on Tris Glycine 4-15% SDS gel (Bio-Rad) in adjacent wells. After electrophoresis, the lanes were separated and stained in Imperial protein stain (Pierce) or silver stain (Pierce) and assayed for Mn oxidation (Francis C A and Tebo B M (2002) supra). The Imperial stained band that corresponded to the Mn oxidation active band was submitted to MS/MS at the OHSU proteomics core.

Mn(III)-PP trapping UV-vis spectra measurements of Mn oxidation reactions with purified oxidase and Na pyrophosphate were performed and fitted as described previously with *Bacillus* sp. SG-1 exosporium (Soldatova A et al, *J Bioinorganic Chem* 17, 1151-1158 (2012)).

X-Ray Absorption Spectroscopy:

Mn oxide materials were harvested as follows: 5 μg of purified protein was added to 100 ml or 1 L 10 mM HEPES pH 7.8, 50 mM NaCl, 100 μM $MnCl_2$. The reaction was shaken overnight at 30° C. The 100 ml reaction was allowed to settle for about 3 days and the 1 L reaction was allowed to settle for about 20 hours before the oxides were siphoned off the bottom, centrifuged at 5000×g for 10 minutes then centrifuged again for 15000×g for 1 minute in microfuge tubes. The oxides were allowed to air dry before packing into A1 sample holders. Samples were secured with kapton tape with lexan covers between the samples to prevent any reduction of Mn induced by the beam during data collection. Mn K-edge EXAFS was collected on transmission mode at SSRL beamline 4-1 with a Si(220) double crystal monochomator and detuned 60%. Energy calibration was done using the pre-edge feature of potassium permanganate (6543.34 eV). Samples were run at 77K using a liquid nitrogen cryostat. Background subtraction and normalization was done with Athena (Ravel B and Newville M, *J Synchrotron Radiation* 12, 537-541 (2005); incorporated by reference herein.)

Activity Assays:

UV-vis spectrum measurements of Mn oxidation reactions with purified oxidase and Na pyrophosphate were performed and fitted as described previously with *Bacillus* sp. SG-1 exosporium (Soldatova A et al 2012 supra and Webb S M et al, 2005 supra.)

Continuous-wave spectrum electron paramagnetic resonance (EPR) was collected at an X-band frequency (9.68 GHz) with a Bruker ER085CS spectrometer. The measurement parameters follow are as follows: temperature 15 K; microwave power 2 mW.

Reduction of recombinant Mn oxidase complex was performed by adding excess dithionite to concentrated protein anaerobically. Excess dithionite was removed by running the sample through a protein desalting column (Thermo) equilibrated with 20 mM HEPES pH 7.8 50 mM NaCl buffer degassed with Ar. The UV-visible absorption spectrum was collected on a Varian Cary 50 spectrophotometer to confirm absence of type I Cu absorbance maximum at 590 nm.

Oxygen consumption was measured on a Rank Brothers LTD model 10 electrode with the polarizing voltage set to 630 mV. The 2 ml water-jacketed reaction cell was kept at 37° C. using a water bath. The instrument was calibrated by taking a zero measurement with Ar purged water and a 100% measurement with atmospheric oxygenated water assuming 214 μM O2 at 3° C. A computer interfaced with the electrode measured 02 every 1 s. Data collection began about 1 min before 10 μL of 1 mg/ml Mnx protein (~24 nM final if mass of recombinant Mn oxidase complex is 211 kDa) was added through the 2 mm diameter opening in the cap and allowed to equilibrate with 37° C. 20 mM HEPES pH 7.8 50 mM NaCl. Another minute of baseline reading was taken before adding 10 μL of various concentrations of $MnCl_2$. The data was plotted Time (min) vs. % $O_2$ remaining, if addition of $MnCl_2$ is t=0. The initial $O_2$ consumption velocities of all runs were plotted against starting $MnCl_2$ concentration. Total $O_2$ consumed was calculated by taking the difference of final from initial $O_2$ concentrations then plotted against $MnCl_2$ concentration and fitted with a linear regression, forced through the xy origin.

Kinetic experiments were performed on the Molecular Devices SpectraMax® M2 microplate reader spectrophotometer at 22° C. with purified protein. 2,2'-azino-bis(3-ethylbenzthiazoline-6-sulphonic acid) (ABTS) oxidation was measured directly at 420 nm using an extinction coefficient of 36 mM-1 cm-1. Reactions were carried out with 10 μg Mnx (final 240 nM) 100 mM in phosphate-citrate buffer pH 3-8 and 20 mM CHES, HEPES, and MES at pH 7-10. Dimethoxyphenol (DMP) oxidation was followed by measuring the increase in absorbance at 468 nm and ϵ=49.6 mM-1 cm-1. These assays were performed in at least two independent trials in triplicate. Fe(II) (ferrous ammonium sulfate) oxidation was measured by quenching 200 μl reactions with 50 μl of the Fe(II) chelating colorimetric assay FerroZine® (15 mM) and a ferrous ammonium sulfate standard curve, noting the absorbance at 570 nm. Fe(II) oxidation reactions were performed with 10 μg recombinant Mn oxidase complex in 100 mM Na acetate-acetic acid buffer (pH 4-5.5). Mn(II) ($MnCl_2$) oxidation in 20 mM HEPES (pH 7-8.5) was measured by quenching 5 μl of 200 μl reactions with 195 μl leucoberbelin blue (LBB) colorimetric reagent and reading the absorbance at 618 nm. Working LBB reagent was prepared by diluting concentrated stock (100 mg LBB in 25 ml 0.4% NaOH) 1:10 into 1% acetic acid. A KMnO4 standard curve was used to determine MnO2 oxide equivalent concentration. The metal substrate assays were performed in five independent trials then the high and low values were discarded from each concentration. The linear part of each curve was fit plotted and fit with a linear regression in GraphPad Prism®. These slopes were converted to the appropriate kinetic units, plotted, and fit with nonlinear regressions determined by comparing best fit values in the same software. $K_M$ and Vmax were determined and reported as $K_M$ and $k_{cat}=V_{max}/[enzyme]$.

The invention claimed is:

1. A method of recombinantly expressing a manganese oxidase complex, the method comprising:

inoculating a culture media comprising at least 0.2 μM copper ion with an *E. coli* bacterium comprising an *E. coli* expression vector, the *E. coli* expression vector comprising a first polynucleotide that encodes a first polypeptide comprising SEQ ID NO: 7 or a homolog with no more than ten conservative amino acid substitution mutations, a second polynucleotide that encodes a second polypeptide selected from SEQ ID NO: 6 or a homolog with no more than ten conservative amino acid substitution mutations and a third polynucleotide that encodes SEQ ID NO: 5 or a homolog with no more than ten conservative amino acid substitution mutations provided that the manganese oxidase complex catalyzes the oxidation of Mn(II) to Mn(IV); and an IPTG inducible promoter operably linked to the first polynucleotide, the second polynucleotide, and the third polynucleotide adding IPTG to the culture media;

adding a copper salt to the culture media to reach a concentration of copper ion of at least 2.0 μM;

agitating the culture media after inoculating the culture media, but before adding the copper salt to the culture media;

and, after adding the copper salt to reach the concentration of copper ion of at least 2.0 μM, incubating the culture media for at least 8 hours without agitation.

2. The method of claim 1, the copper salt comprising $CuSO_4$.

3. The method of claim 1, further comprising purifying the manganese oxidase complex.

4. The method of claim 3 further comprising purifying the complex by FPLC.

5. The method of claim 1, the manganese oxidase complex comprising a protein tag covalently attached to a component of the complex.

6. The method of claim 5 further comprising purifying the complex using the protein tag.

7. The method of claim 1 comprising incubating the culture for at least 22 hours without agitation.

8. The method of claim 1, where the expression vector further comprises a fourth polynucleotide operably linked to the IPTG inducible promoter that encodes a polypeptide of SEQ ID NO: 4 or a homolog with no more than ten conservative amino acid substitution mutations.

* * * * *